(12) United States Patent
Waligora et al.

(10) Patent No.: US 9,145,431 B2
(45) Date of Patent: Sep. 29, 2015

(54) SYNTHESIS AND FORMULATIONS OF SALTS OF ISOPHOSPHORAMIDE MUSTARD AND ANALOGS THEREOF

(71) Applicants: Frank W. Waligora, Haverhill, MA (US); John C. Amedio, Jr., Franklin, MA (US)

(72) Inventors: Frank W. Waligora, Haverhill, MA (US); John C. Amedio, Jr., Franklin, MA (US)

(73) Assignee: ZIOPHARM Oncology, Inc., Boston, MA (US)

( * ) Notice: Subject to any disclaimer, the term of this patent is extended or adjusted under 35 U.S.C. 154(b) by 0 days.

(21) Appl. No.: 14/167,169

(22) Filed: Jan. 29, 2014

(65) Prior Publication Data

US 2014/0378704 A1 Dec. 25, 2014

Related U.S. Application Data

(63) Continuation of application No. 13/056,628, filed as application No. PCT/US2009/052295 on Jul. 30, 2009, now Pat. No. 8,664,201.

(60) Provisional application No. 61/137,538, filed on Jul. 31, 2008.

(51) Int. Cl.
| | |
|---|---|
| C07F 9/22 | (2006.01) |
| A61K 31/66 | (2006.01) |
| A61K 31/675 | (2006.01) |
| C07F 9/20 | (2006.01) |
| C07F 9/24 | (2006.01) |

(52) U.S. Cl.
CPC . *C07F 9/22* (2013.01); *A61K 31/66* (2013.01); *A61K 31/675* (2013.01); *C07F 9/20* (2013.01); *C07F 9/222* (2013.01); *C07F 9/2429* (2013.01); *C07F 9/2458* (2013.01)

(58) Field of Classification Search
USPC .......................................................... 564/14
See application file for complete search history.

(56) References Cited

U.S. PATENT DOCUMENTS

| | | | |
|---|---|---|---|
| 5,530,020 A | 6/1996 | Gunawardana et al. | |
| 5,912,264 A | 6/1999 | Wittman et al. | |
| 6,197,760 B1 | 3/2001 | Struck | |
| 6,610,860 B2 | 8/2003 | Holton | |
| 8,664,201 B2 | 3/2014 | Waligora et al. | |
| 2006/0089333 A1 | 4/2006 | Morgan | |

FOREIGN PATENT DOCUMENTS

| | | |
|---|---|---|
| SU | 427945 A1 | 5/1974 |
| WO | WO-2004018478 A2 | 3/2004 |
| WO | WO-2006/047575 A2 | 5/2006 |
| WO | WO-2008124097 A2 | 10/2008 |
| WO | WO-2010014841 A1 | 2/2010 |

OTHER PUBLICATIONS

Han, S.Y. et al. "Synthesis of 17O (and 18O) Labelled Isophosphoramide Mustard," Journal of Labelled Compounds and Radiopharmaceuticals (1994) vol. XXXIV No. 3 pp. 247-254.*
Cancer [online], [retrieved on Jul. 6, 2007] Retrieved from the Internet, URL: http://www.nlm.nih.gov/medlineplus/cancer.html.
Chemical Abstracts Accession No. 81.37378 & SU 427945 A1 (Institute of Heteroorganic Compounds) May 15, 1974 (1 page).
Extended European Search Report for European Patent Application No. 09803607.2 mailed Jun. 25, 2013. 9 pages.
Golub et al., Molecular Classification of Cancer: Class Discovery and Class Prediction by Gene Expression Monitoring, Science (1999), vol. 286, 531-537.
International Search Report and Written Opinion dated Nov. 10, 2009 for corresponding International Patent Application No. PCT/US2009/052295 (14 pages).
Lala et al., Role of nitric oxide in tumor progression: Lessons from experimental tumors, Cancer and Metastasis Reviews (1998), 17, 91-106.
Misiura, K. et al., Isophoshoramide mustard analogues as prodrugs for anti-cancer gene-directed enzyme-prodrug therapy (GDEP) Acta Biochimica Polonica (2002) vol. 49, No. 1 pp. 169-176.
Noyori, Ryoji et al. "Toward Efficient Asymmetric Hydrogenation: Architectural and Functional Engineering of Chiral Molecular Catalysts." PNAS. Apr. 13, 2004. vol. 101, No. 15, pp. 5356-5362. 7 pages.
Remington, "The Science and Practice of Pharmacy," vol. I, 19th Edition, Mack Publishing Company, Easton, Pennsylvania, 1995, ISBN 0-912734-04-3, 10 pages.
Remington, "The Science and Practice of Pharmacy," vol. II, 19th Edition, Mack Publishing Company, Easton, Pennsylvania, 1995, ISBN 0-912734-04-3, 1, 7 pages.
Written Opinion dated Feb. 6, 2012 for corresponding Singapore Patent Application No. 201100673-1 (8 pages).
Zakharov, S. et al. "Catalytic phosphorylation of polyfluoroalkanols. Communication 5. Catalytic phosphorylation of .alpha.-polyfluoroalkylbenzyl alcohols with phosphoryl chloride" Bulletin of the Academy of Sciences of the USSR (1976) vol. 25, No. 8, pp. 1727-1731 (English language) & Institute of Heteroorganic Compounds (1976) No. 8, pp. 1834-1837 (Russian language).

* cited by examiner

*Primary Examiner* — Kristin Vajda
(74) *Attorney, Agent, or Firm* — Wilmer Cutler Pickering Hale and Dorr LLP

(57) ABSTRACT

Disclosed herein are formulations and methods of manufacture of compounds of formula (E):

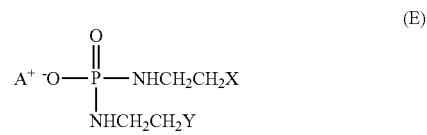

wherein X and Y independently represent leaving groups; and $A^+$ is an ammonium cation.

15 Claims, No Drawings

SYNTHESIS AND FORMULATIONS OF SALTS OF ISOPHOSPHORAMIDE MUSTARD AND ANALOGS THEREOF

CROSS REFERENCE TO RELATED APPLICATIONS

This application is a continuation of U.S. application Ser. No. 13/056,628, filed May 23, 2011, which was the national stage filing under 35 U.S.C. §371 of PCT application PCT/US2009/052295 filed Jul. 30, 2009, which claims the benefit of U.S. Provisional Application Ser. No. 61/137,538 filed Jul. 31, 2008, all of which are incorporated by reference herein in their entirety. PCT/US2009/052295 was published under PCT Article 21(2) in English.

BACKGROUND

Autopsies of soldiers killed by mustard gas in World War I indicated that sulfur mustard has a disproportionate effect on rapidly dividing cells and suggested that sulfur mustard compounds might have antitumor effects. Indeed, early researchers attempted to treat cancer by direct injection of sulfur mustard into tumors. This research was limited by the extreme toxicity of sulfur mustard compounds and nitrogen mustard analogs, such as mechlorethamine, were investigated as less toxic alternatives.

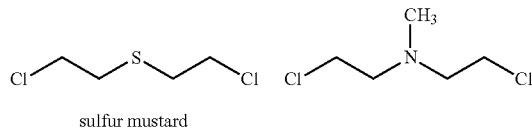

sulfur mustard

Because of the lack of selectivity of most mechlorethamine analogs, prodrugs, such as phosphoramide compounds, which can be activated by the high concentration of phosphoramidases present in neoplastic cells, have been investigated. Two phosphoramide alkylating agents, cyclophosphamide (CPA) and the isomeric compound ifosfamide (IFOS), have demonstrated effectiveness in the treatment of a broad range of solid tumors and hematological cancers (Zhang et al., Current Drug Therapy 1: 55-84 (2006)). CPA and IFOS are used both as single agents as well as in combination with other anticancer agents to obtain synergistic antitumor effects. In addition to its application in cancer, CPA can also be used as an immunosuppressant to treat autoimmune diseases such as rheumatoid arthritis and systemic lupus erythematosus (SLE) (Petri et al., Lupus 13:366-371 (2006); Leandro et al. Ann., Rheum. Dis. 61: 883-888 (2002); Verberg et al., Arthritis Rheum. 52: 421-424 (2005)).

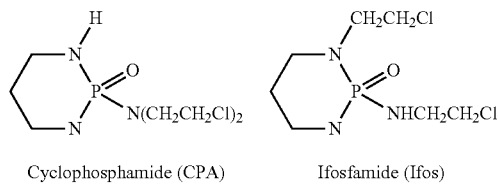

Cyclophosphamide (CPA)   Ifosfamide (Ifos)

The metabolism of CPA and IFOS has been described in detail by Zhang et al. (Zhang et al., Current Drug Therapy 1: 55-84 (2006)). CPA and IFOS are prodrugs that are activated intracellularly by 4-hydroxylation by the cytochrome (CYP) P450 oxidases, primarily CYP3A4, CYP2C9 and CYP2B6 in the liver, to produce cytotoxic nitrogen mustards that can react with DNA. Acrolein is a byproduct of this reaction. The in vivo metabolism of CPA and IFOS also involves inactivation by N-decholoroethylation by CYP3A4/5 and CYP2B6 prior to their conversion to the nitrogen mustards, resulting in production of dechloroethylated metabolites and the byproduct chloroacetaldehyde (CAA). Acrolein and CAA are implicated in toxicities of CPA and IFOS that are unrelated to the cytotoxic mechanism of action of the nitrogen mustard molecules (Zhang et al., Current Drug Therapy 1: 55-84 (2006)). Acrolein causes the urotoxicity, hemorrahagic cystitis, and liver damage, and CAA causes neurotoxicity and has also been implicated in renal toxicity. Co-administration of the sulfhydryl compounds, mesna and amifostine, which react specifically with acrolein in the urinary tract, can reduce the urotoxicity of acrolein but does not eliminate other toxicities (Zaki et al., Toxicol. In Vitro 17: 397-402 (2003)).

The nitrogen mustards of CPA and IFOS, phosphoramide mustard and isophosphoramide mustard, are bifunctional alkylating agents that bind covalently to nucleophilic groups of nucleic acids. At pH≥7, the mustards are dechlorinated to produce carbonium ions that react covalently with $N^7$ of guanine residues. The reaction is referred to as DNA alkylation. Both inter- or intra-strand crosslinks result from the ability of each mustard molecule to react with two guanine residues (Zhang et al., Current Drug Therapy 1: 55-84 (2006)). Because the inter-strand crosslinks prevent strand separation required for DNA replication, DNA-alkylation is considered to be the major mechanism responsible for the inhibition of cell division by CPA and IFOS. In addition to the antiproliferative (cytostatic) effect, the DNA damage also induces apoptosis, i.e., programmed cell death (O'Conner et al., Cancer Res. 1: 6550-6557; (1991); Bahtia et al., Clin. Cancer Res. 1: 873-880 (1995)). The cytotoxic/cytostatic effects of the nitrogen mustards are mainly responsible for the antitumor activity of CPA and IFOS and, by preventing the proliferative expansion of autoreactive lymphocytes, also for the immunosuppressant activity of CPA in autoimmune disease. However, cross-linking of DNA in normal tissues by the nitrogen mustards also causes cytotoxic, mechanism-based collateral damage, particularly myelosuppression resulting in leucocytopenia, which is the principal dose-limiting hematological toxicity (Zhang et al., Current Drug Therapy 1: 55-84 (2006)).

Although phosphoramide mustard and isophosphoramide are chemically similar, isophosphoramide mustard interacts with DNA with a higher affinity than phosphoramide mustard (Boal et al., J. Med. Chem. 32: 1768-1773; 1989). Structural differences involving the intramolecular distance between the chloroethyl groups and their orientation appear to be responsible for the different affinities of the two mustards (Springer et al., J. Org. Chem. 63: 7218-7222 (1998)).

By administering cytotoxic nitrogen mustards directly to cancer patients, the "off-target" toxicities and the drug resistance associated with the prodrugs may be reduced. IPM has been synthesized and preliminary biological evaluations of the compound have been conducted; but, unfortunately, IPM itself is unstable and difficult to use directly for human treatment. Stabilized formulations of IPM might further reduce toxicity and allow metronomic administration of doses that are sufficient for both direct cytotoxicity against the tumor and antiangiogenic activity. Improved methods for formulation and manufacture of IPM and analogues and salts thereof are needed.

SUMMARY

The invention discloses pharmaceutical formulations of isophosphoramide mustard (IPM) salts and analogues thereof as well as methods for synthesizing IPM and salts and analogues thereof. IPM salts and analogues of the invention include compounds of formula (E):

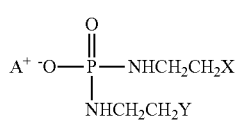
(E)

wherein X and Y independently represent leaving groups; and $A^+$ is an ammonium cation.

In certain embodiments, the invention relates to pharmaceutical formulations comprising a compound of formula (E) and one or more pharmaceutically acceptable carriers. Methods of preparing such compounds and formulations are also described.

DETAILED DESCRIPTION

The disclosure concerns pharmaceutical formulations of isophosphoramide mustard (IPM) salts and analogues thereof as well as methods for synthesizing IPM and salts and analogues thereof. IPM salts and analogues of the invention include compounds of formula (E):

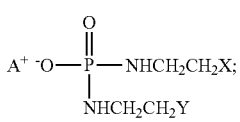
(E)

wherein X and Y independently represent leaving groups such as Cl, Br, I, or a sulfonate, e.g., toluenesulfonate, methanesulfonate, 2,4,6-triisopropylbenzenesulfonate, or 2,4,6-trimethylbenzenesulfonate; and $A^+$ is an ammonium cation. Compounds disclosed in U.S. application Ser. No. 11/257,766, filed Oct. 25, 2005 are useful in the compositions and methods of the invention and are herein incorporated by reference. Formulations of the invention include IPM salts and analogues together with a lubricant, a diluent and a disintegrant. Formulations of the invention may further comprise additional excipients such as a binder and a compression filler. The disclosure further concerns the synthetic preparation of IPM salts and analogues thereof.

I. Salts of IPM and IPM Analogs

The formulations disclosed herein include IPM and IPM analogs that are formulated with one or more equivalents of base. In certain embodiments, the disclosed compounds are salts of isophosphoramide mustard or isophosphoramide mustard analogs including one or more cations. In one embodiment, the cations can be a conjugate acid of an amine base or can be a quaternary ammonium cation. Suitable counterions for isophosphoramide and its analogs include the conjugate acids (as used herein, terms that refer to amines should be understood to include their conjugate acids unless the context indicates that the free amine is intended) of bases including basic amino acids, aliphatic amines, heterocyclic amines, aromatic amines, pyridines, guanidines, and amidines.

In certain embodiments, group A of formula (E):

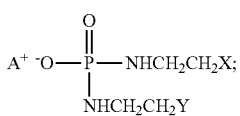
(E)

is selected from a primary, secondary or tertiary amine. For example, in certain embodiments, A of formula (E) represents at least one primary amine such as lysine, arginine, alanine, asparagine, aspartic acid, cysteine, glutamic acid, glutamine, glycine, histidine, isoleucine, leucine, lysine, methionine, phenylalanine, serine, threonine, tryptophan, tyrosine, valine, 2-aminoethanol, or tris(hydroxymethyl)aminomethane. In certain embodiments, A of formula (E) represents at least one secondary amine such as diethylamine, 2-(methylamino) ethanol, aziridine, azetidine, pyrrolidine and piperidine. In certain embodiments, A of formula (E) represents at least one tertiary amine, such as triethylamine, trimethylamine, N, N-diisopropylethylamine, and 2-(dimethylamino)ethanol.

Primary, secondary, and tertiary amine as used herein refers to the number of direct single bonds between a nitrogen and carbon atom(s), the remainder of the three valencies of the neutral amine being filled by hydrogen atoms. A primary amine has only one direct bond between nitrogen and carbon, while a secondary amine is singly bound to exactly two carbons, a tertiary amine is singly bound to exactly three carbons. Quarternary ammonium cations have four single bonds to carbon atoms, the fourth bond involving the lone pair of the nitrogen atom as well as the three valencies ordinarily present in primary, secondary, and tertiary amines. Accordingly, as the name implies, such species carry a positive charge. In order for a molecule to be classified within a particular amine type, e.g., primary, secondary or tertiary amine, the molecule must comprise at least one nitrogen with the indicated bonding pattern to carbon(s). For example, a primary amine comprises at least one nitrogen that is singly bound to exactly one carbon atom. A molecule may however comprise more than one type of amine, e.g., 2-aminopiperidine comprises both primary and secondary amine functionality.

In certain embodiments, the amine is an aliphatic amine, such as an acyclic aliphatic amine. In certain embodiments, the amine is an acyclic aliphatic amine, e.g., an amine having 2-3 branched or straight chain alkyl substituents. In certain embodiments, each branched or straight chain alkyl substituent is a $C_3$-$C_{10}$ alkyl amine, such as a $C_3$-$C_5$ alkyl amine. In certain such embodiments, one or more of the branched or straight chain alkyl substituents are optionally substituted, such as with one or more hydroxyl substituents, e.g., 1, 2, 3 or 4 hydroxyl substituents.

Exemplary amines (and their corresponding ammonium ions) for use in the formulations or methods of the invention include pyridine, N, N-dimethylaminopyridine, diazabicyclononane, diazabicycloundecene, N-methyl-N-ethylamine, diethylamine, triethylamine, N, N-diisopropylethylamine, mono-, bis-, or tris-(2-hydroxyethyl)amine, 2-hydroxy-tert-butylamine, tris(hydroxymethyl)methylamine, N, N-dimethyl-N-(2-hydroxyethyl)amine, tri-(2-hydroxyethyl)amine and N-methyl-D-glucamine.

In a further aspect, the salts described above in formula (E) can include a second amine or ammonium group. In certain embodiments, the compounds disclosed herein include more than one equivalent of an amine for each equivalent of isophosphoramide mustard or isophosphoramide mustard analog. Such embodiments include those having non-integer ratios of amine to isophosphoramide mustard or isophosphoramide mustard analogs. In certain embodiments, the compounds have a two to one or three to one ratio of amine to isophosphoramide mustard or an isophosphoramide mustard analog. In working embodiments, salts were produced containing two equivalents of amine base per equivalent of isophosphoramide mustard. In some embodiments, an amine base used to form isophosphoramide mustard and isophosphoramide mustard analog salts includes more than one amino group; such bases can be termed "multibasic." More specifically, certain examples of multibasic bases that can be used have two amino groups; such compounds can be referred to as "dibasic." For example, one suitable dibasic molecule is N,N-dimethylaminopyridine, which includes two basic amino groups. In a particular embodiment of a compound disclosed herein, a compound includes isophosphoramide mustard or an isophosphoramide mustard analog and one equivalent of a dibasic amine.

In one embodiment, the disclosed compounds include one or more zwitterionic bases. Examples of such bases include basic amino acids, which are zwitterionic at physiological pH.

As used herein, "aliphatic amine" refers to a compound of the formula $NR^1R^2R^3$, wherein at least one of $R^1$, $R^2$ or $R^3$ is an aliphatic group.

The term "acyclic aliphatic amine" refers to an aliphatic amine as above, wherein at least one, and preferably all, of the aliphatic groups is acyclic.

The term "heterocyclic amine" refers to a compound of the formula $NR^1R^2R^3$, wherein at least one of $R^1$, $R^2$ or $R^3$ is a heterocyclic group or $R^1$, $R^2$ and/or $R^3$ taken together with their common nitrogen atom form a ring.

The term "leaving group" refers to a group that can be displaced by a nucleophile. With reference to the presently disclosed compounds, leaving group refers to a group that can be displaced to form an aziridinium intermediate, or can be directly displaced by a biomolecular nucleophile, such as a nucleic acid nucleophile, to form, for example, a 7-alkylated guanidinium species. Examples of suitable leaving groups include the halogens and the sulfonates (—$SO_2R$). In certain embodiments, for the isophosphoramide analog salts disclosed herein, the compound is a "mixed" leaving group compound, including two different types of leaving groups, for example a halogen and a sulfonate or two different halogens, such as a bromide and a chloride. U.S. Pat. No. 6,197,760 to Struck teaches methods for making such mixed leaving group compounds.

II. Formulation of IPM Salts and Analogues Thereof

An aspect of the disclosure includes pharmaceutical formulations, such as an oral dosage form, prepared for administration to a subject and which include a therapeutically effective amount of one or more of the IPM salts and analogues thereof disclosed herein or elsewhere. The formulation may be in the form of a pill, a tablet or a capsule to be administered orally. In certain embodiments, the formulation is in the form of a capsule for oral administration.

In certain embodiments, the formulation comprises a lubricant, a diluent and a disintegrant in addition to, e.g., admixed with, the IPM salt or analogue thereof. The formulation may comprise, for example, 0.25-5% of a lubricant, up to 98% of a diluent such as from 80 to 98%, such as 85 to 95% such as about 90% of a diluent, and up to 90% of a disintegrant such as from 0.5 to 10%, such as from 0.5 to 5%, such as about 1% of a disintegrant by weight of the formulation. The formulation may further comprise one or more additional diluents, disintegrants or lubricants and additional carriers.

In certain embodiments, an oral dosage form comprises from 1 to 250 mg of the compound of formula (E) such as from about 1 to about 100 mg or from about 10 mg to about 50 mg. In certain embodiments, the formulation comprises from 5-25 mg of the compound of formula (E) such as about 5 mg, about 7.5 mg, about 10 mg, about 12 mg, about 15 mg, about 20 mg and about 25 mg. In certain embodiments, the compound of formula (E) is the tris(hydroxymethyl)aminomethane (Tris) salt:

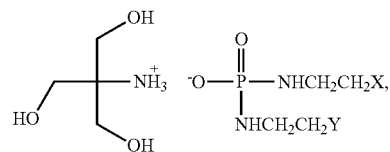

wherein X and Y are independently selected from leaving groups, such as Cl, Br, or I, or a sulfonate, e.g., toluenesulfonate, methanesulfonate, 2,4,6-triisopropylbenzenesulfonate, or 2,4,6-trimethylbenzenesulfonate.

In certain embodiments, the lubricant of the formulation may be selected from any one or more of talc; fumed silicon dioxide such as Aerosil, Cab-O-Sil, or Syloid; starch; calcium silicate; magnesium carbonate (heavy); magnesium oxide (heavy); magnesium lauryl sulfate, sodium lauryl sulfate, calcium stearate, sodium stearyl fumarate, polyethylene glycol 4000 and 6000, sodium benzoate, light mineral oil, hydrogenated vegetable oils, stearic acid, or glyceryl behenate. In certain embodiments, the lubricant is magnesium stearate. In certain embodiments, the lubricant of the formulation comprises the salt of a fatty acid, such as the salt of a long chain, e.g., $C_{10}$-$C_{24}$, saturated or unsaturated fatty acid. In certain embodiments, the salt of a fatty acid is a metallic salt, such as the magnesium salt of a fatty acid, e.g., magnesium stearate. In certain embodiments, the lubricant of the formulation comprises a long chain fatty acid ester such as sodium stearyl fumarate. In other embodiments, the lubricant comprises a mixture of glycerides of fatty acids such as glyceryl behenate.

The formulation may comprise at least one of the following lubricants in the indicated amount (by weight of the formulation):

| | |
|---|---|
| Talc | 1-5%, |
| Fumed silicon dioxide | 0.1-0.5%, |
| Starch | 1-10%, |
| Calcium silicate | 0.5-2.0%, |
| Magnesium carbonate (heavy) | 1-3%, |
| Magnesium oxide (heavy) | 1-3%, |
| Magnesium lauryl sulphate | 0.2-2%, |
| Sodium lauryl sulphate | 0.2-2%, |
| Calcium stearate | 0.5-4%, |
| Sodium stearyl fumarate | 0.5-2%, |
| Polyethylene glycol 4000 and 6000 | 2-10%, |
| Sodium benzoate | 2-5%, |
| Light mineral oil | 1-3%, |
| Hydrogenated vegetable oils | 1-5%, |
| Stearic acid | 0.25-2%, and |
| Glyceryl behenate | 0.5-4%. |

In certain embodiments, the formulation comprises magnesium stearate in an amount (by weight of formulation) selected from 0.25% and 2% or from 0.25% to 1% or about 0.5%.

The capsule formulation may comprise a diluent selected from any one or more of lactose, microcrystalline cellulose, mannitol, calcium hydroxy-dioxido-oxo-phosphorane, dextrose, glucose, sucrose, starch and derivatives, calcium carbonate, dicalcium phosphate and magnesium carbonate. In certain embodiments, the diluent is selected from microcrystalline cellulose, mannitol, lactose and calcium hydroxydio-dioxido-oxo-phosphorane. In certain embodiments, the diluent is microcrystalline cellulose.

In certain embodiments, the diluent comprises a carbohydrate, such as sugar or sugar alcohols (e.g., lactose, α-lactose monohydrate, sucrose, mannitol, or sorbitol), or a cellulose polymer such as microcrystalline cellulose, silicified microcrystalline cellulose, or powdered cellulose.

The formulation may comprise at least one diluent in an amount up to 98% by weight of the formulation such as from about 50-85% or about 50-75%. In certain exemplary embodiments, the formulation comprises one or more of the following diluents in the indicated amount by weight of the formulation:

| | |
|---|---|
| microcrystalline cellulose | 5-98%, |
| mannitol | 10-90%, |
| dextrose | up to 98%, |
| glucose | up to 98%, |
| starch and derivatives | up to 98%, |
| calcium carbonate | up to 98%, |
| dicalcium phosphate | up to 98%, |
| magnesium carbonate | up to 98%, |
| lactose | up to 98% and |
| calcium hydroxydiodioxido-oxo-phosphorane | 10-80%. |

In certain embodiments, the formulation comprises from 85-95% microcrystalline cellulose. The formulation may comprise from 88-92% microcrystalline cellulose such as about 91% microcrystalline cellulose. In exemplary embodiments, the formulation comprises 0.25-1% magnesium stearate and about 91% microcrystalline cellulose. In certain particular embodiments, the formulation comprises about 91% microcrystalline cellulose and about 0.5% magnesium stearate.

The formulation may comprise at least one disintegrant, e.g., a water-soluble polymer, preferably an anionic water-soluble polymer, such as cellulose or a derivative thereof or a salt thereof. In various embodiments, the disintegrant may be selected from any one or more of starch, microcrystalline cellulose, insoluble ion exchange resins, sodium starch glycolate, sodium carboxymethylcellulose, gums such as agar, guar and xanthan, alginic acid, sodium alginate and povidone. In certain embodiments, the disintegrant comprises a salt of cellulose or a derivative thereof. Derivatives of cellulose include molecules in which one or more of the hydroxyl functionalities of cellulose are bound to atoms or groups of atoms other than hydrogen. For example, the disintegrant may comprise carboxymethylcellulose (CMC) (e.g., a cellulose derivative with carboxymethyl groups (—CH$_2$—COOH) bound to some of the hydroxyl groups of the glucopyranose monomers that make up the cellulose backbone) or an anionic form thereof. In certain embodiments, the disintegrant is or comprises sodium carboxymethylcellulose, which may optionally be crosslinked. Preferably, the disintegrant is selected such that the formulation disintegrates in the stomach in less than 30 minutes, such as less than 15 minutes, or even less than 10 minutes.

The formulation may comprise at least one disintegrant in an amount up to 90% by weight of the formulation. In certain exemplary embodiments, the formulation comprises one of the following disintegrants in the indicated amount by weight of the formulation:

| | |
|---|---|
| microcrystalline cellulose | 5-90%, |
| starch | 3-25%, |
| sodium starch glycolate | 2-8%, |
| sodium carboxymethylcellulose | up to 15%, |
| gum | less than 5% |
| alginic acid or sodium alginate | 4-6%, and |
| crospovidone | 1-5%. |

In certain embodiments, the disintgrant is sodium carboxymethylcellulose. The formulation may comprise from 0.5-2% sodium carboxymethylcellulose. In certain embodiments, the formulation comprises about 1% sodium carboxymethylcellulose. In certain embodiments, the formulation comprises 0.5-2.0% sodium carboxymethylcellulose, 0.25-1% magnesium stearate, at least about 90% microcrystalline cellulose, and from 5-9% of the compound of formula (E). In exemplary embodiments, the formulation comprises about 1% sodium carboxymethylcellulose, about 91% microcrystalline cellulose, about 0.5% magnesium stearate and about 15 mg of the compound of formula (E):

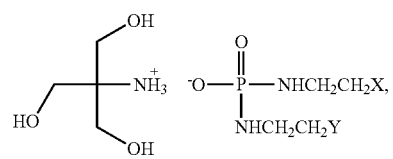

wherein X and Y are leaving groups, such as Br, Cl, or I. In an exemplary embodiment, the compound of formula (E) is:

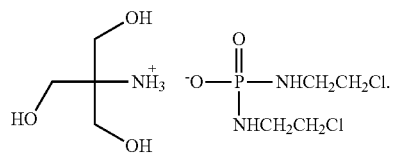

The formulation may further comprise one or more additional carriers such as a binder from 3-90% and a compression filler up to 98%. The formulation may further comprise a carrier selected from a second diluent, a second disintegrant, and a second lubricant. Other pharmaceutically acceptable carriers useful for these formulations are conventional. *Remington's Pharmaceutical Sciences*, by E. W. Martin, Mack Publishing Co., Easton, Pa., 19th Edition (1995), describes formulations suitable for pharmaceutical delivery of the compounds herein disclosed.

In certain embodiments, the formulation comprises a component that performs the function of two or more of a lubricant, a diluent, and a disintegrant, e.g., acts as both a lubricant and a disintegrant. For example, the formulation may comprise microcrystalline cellulose as both the diluent and the disintegrant. In certain such embodiments, there may or may not be one or more additional diluents and/or disintegrants in a formulation, and/or the multi-acting component is present in an amount equal to the amounts of all of the components whose functions it performs. In certain embodiments, a single component of the formulation may act as all three of a diluent, a lubricant and a disintegrant. In certain embodiments, each of a lubricant, diluent and disintegrant are compounds that are distinct from one another.

Pharmaceutical formulations can also include one or more additional active ingredients such as antimicrobial agents, anti-inflammatory agents, anesthetics, and the like.

In one aspect, certain embodiments of pharmaceutical formulations are formulated into unit dosage forms. For example such unit dosage forms can contain from about 1 mg to about 250 mg, such as from about 5 mg to about 100 mg, such as about 5 mg to about 50 mg, such as about 5 mg, about 10 mg, about 15 mg, about 20 mg, about 25 mg, about 30 mg, about 35 mg, about 40 mg, about 45 mg or about 50 mg of a disclosed isophosphoramide mustard salt or analog thereof per dosage unit.

In certain embodiments, the formulations of IPM salts or analogs thereof disclosed herein, are stable at room temperature for at least two weeks, at least one month, at least two months at 5° C., at least three months at 5° C., at least six months at 5° C., at least 9 months at 5° C., at least 12 months at 5° C., at least 18 months at 5° C., or even at least 24 months at 5° C. In certain embodiments, the active ingredient of such stable formulations undergoes less than 10% decomposition, preferably less than 5%, 2%, or even less than 1% decomposition, e.g., as measured by assaying for the presence of decomposition by-products such as phosphoric acid and its salts and substituted ethylamines, such as by HPLC or GC, for at least two weeks, at least one month, at least two months, at least three months, or even at least six months. In other embodiments, the stable formulations maintain >90%, >95%, or even >98% potency at room temperature for at least two weeks, at least one month, at least two months at 5° C., at least three months at 5° C., at least six months at 5° C., at least 9 months at 5° C., at least 12 months at 5° C., at least 18 months at 5° C., or even at least 24 months at 5° C., e.g., as determined by HPLC analysis.

As used herein, the term "stable" means that the purity of the IPM salt or analog thereof after a period of time (e.g., one month, two months, three months, six months, one year, etc.) is at least 90%, at least 95%, at least 97%, or even at least 99% of the initial purity, which may be determined e.g., by HPLC using evaporative light scattering detection (ELSD). Such an assay may be performed, for example, using a C18 column and an isocratic system with a mobile phase comprising 0.005 M heptafluorobutyric acid and 0.1% trifluoroacetic acid in water.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with carriers. In soft capsules, the active compounds may be dissolved or suspended in suitable liquids, such as fatty oils, liquid paraffin, or liquid polyethylene glycols (PEGs). In addition, stabilizers may be added.

Methods are disclosed herein for treating conditions characterized by abnormal or pathological proliferative activity or neoplasia by administering one or more of the disclosed compounds or formulations to a subject. "Neoplasia" refers to the process of abnormal and uncontrolled cell growth. Neoplasia is one example of a proliferative disorder. The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant."

Conditions that can be treated according to the disclosed method include those characterized by abnormal cell growth and/or differentiation, such as cancers and other neoplastic conditions. Typical examples of proliferative disorders that can be treated using the disclosed compounds and formulations are listed below.

Examples of hematological tumors that can be treated using the compounds and formulations disclosed herein include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Additional examples of conditions that can be treated using the disclosed compounds and formulations include solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). In certain embodiments, the lung cancer is non-small cell or small cell lung cancer.

In certain embodiments, the methods disclosed herein include treating a subject having a CPA-resistant neoplastic condition with an isophosphoramide mustard salt or analog thereof as disclosed herein.

In one embodiment of the method a subject is administered from about 0.2 mg/kg/day to about 20 mg/kg/day of a disclosed isophosphoramide mustard salt or analog thereof. For example, from about 0.5 to about 10 mg/kg/day, such as from about 1 to about 7.5 mg/kg/day of a disclosed compound can be administered to a subject.

In another embodiment of the method, a subject is administered from about 10 to about 700 mg/m$^2$/day, such as from about 20 to about 400 mg/m$^2$/day or from about 100 to about 500 mg/m$^2$/day. For example, from about 30 to about 100 mg/m$^2$/day, such as from about 40 to about 90 mg/m$^2$/day of a compound disclosed herein.

In one embodiment of the method for treating hyperproliferative disorders disclosed herein, a disclosed compound is administered to a subject on a multiple daily dosing schedule. In such embodiments the compound is administered on at least two days and on as many as five different days. In one aspect of multiple daily dosing schedules, the compound is administered to the subject on consecutive days, such as from two to five consecutive days.

In one embodiment of the method one or more additional therapeutic agents is administered to a subject in addition to the presently disclosed compounds and formulations. For example, additional therapeutic agents can that can be used include microtubule binding agents, DNA intercalators or cross-linkers, DNA synthesis inhibitors, DNA and/or RNA transcription inhibitors, antibodies, enzymes, enzyme inhibitors, gene regulators, and/or angiogenesis inhibitors.

"Microtubule binding agent" refers to an agent that interacts with tubulin to stabilize or destabilize microtubule formation thereby inhibiting cell division. Examples of microtubule binding agents that can be used in conjunction with the presently disclosed isophosphoramide mustard salts and analogs thereof include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and will be known to those of ordinary skill in the art. For example, suitable epothilones and epothilone analogs for incorporation into the present compounds are described in International Publication No. WO 2004/018478, which is incorporated herein by reference. Taxoids, such as paclitaxel and docetaxel are currently believed to be particularly useful as therapeutic agents in the presently disclosed compounds. Examples of additional useful taxoids, including analogs of paclitaxel are taught by U.S. Pat. No. 6,610,860 to Holton, U.S. Pat. No. 5,530,020 to Gurram et al. and U.S. Pat. No. 5,912,264 to Wittman et al. Each of these patents is incorporated herein by reference.

Suitable DNA and/or RNA transcription regulators, including, without limitation, actinomycin D, daunorubicin, doxorubicin and derivatives and analogs thereof also are suitable for use in combination with the presently disclosed compounds.

DNA intercalators and cross-linking agents that can be incorporated into the disclosed compounds include, without limitation, cisplatin, carboplatin, oxaliplatin, mitomycins, such as mitomycin C, bleomycin, chlorambucil, cyclophosphamide and derivatives and analogs thereof.

DNA synthesis inhibitors suitable for use as therapeutic agents include, without limitation, methotrexate, 5-fluoro-5'-deoxyuridine, 5-fluorouracil and analogs thereof.

Examples of suitable enzyme inhibitors for use in combination with the presently disclosed compounds include, without limitation, camptothecin, etoposide, formestane, trichostatin and derivatives and analogs thereof.

Suitable therapeutics for use with the presently disclosed compounds that affect gene regulation include agents that result in increased or decreased expression of one or more genes, such as, without limitation, raloxifene, 5-azacytidine, 5-aza-2'-deoxycytidine, tamoxifen, 4-hydroxytamoxifen, mifepristone and derivatives and analogs thereof.

The term "angiogenesis inhibitor" is used herein, to mean a molecule including, but not limited to, biomolecules, such as peptides, proteins, enzymes, polysaccharides, oligonucleotides, DNA, RNA, recombinant vectors, and small molecules that function to inhibit blood vessel growth. Angiogenesis is implicated in certain pathological processes, such as those involved in disorders such as diabetic retinopathy, chronic inflammatory diseases, rheumatoid arthritis, dermatitis, psoriasis, stomach ulcers, and most types of human solid tumors.

Angiogenesis inhibitors are known in the art and examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thrombospondin, endostatin, thalidomide, and derivatives and analogs thereof.

Other therapeutic agents, particularly anti-tumor agents, that may or may not fall under one or more of the classifications above, also are suitable for administration in combination with the presently disclosed compounds. By way of example, such agents include adriamycin, apigenin, rapamycin, zebularine, cimetidine, and derivatives and analogs thereof.

III. Preparation of IPM Salts and Analogues Thereof

In one aspect, the methods are used to prepare compounds of Formula (E):

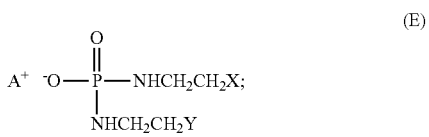

or any salt, prodrug, tautomer, or isomer thereof, wherein:
X and Y independently represent leaving groups; and
$A^+$ is an ammonium cation.

In certain embodiments, the present disclosure provides methods for preparing compounds of Formula (E) via the pathway in Scheme 1.

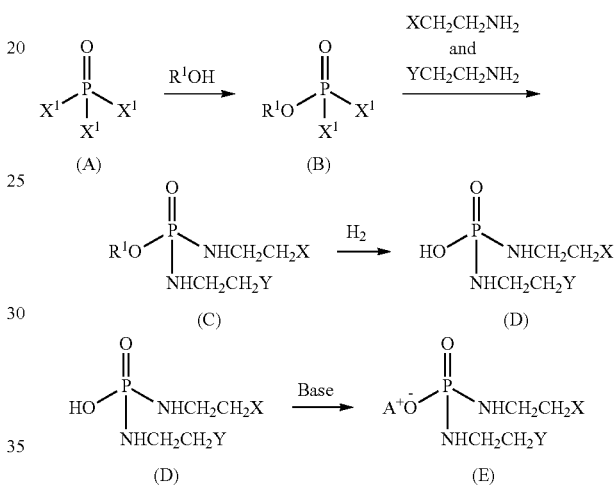

According to Scheme 1, phosphine oxide (A) is treated with alcohol $R^1OH$ affording monoester (B). Monoester (B) is treated with one or more amines, e.g., $XCH_2CH_2NH_2$ and $YCH_2CH_2NH_2$ or salts thereof in concert or in series, under condensation conditions affording phosphordiamidate (C). Phosphordiamidate (C) is converted under hydrogenolysis conditions to phosphordiamidic acid (D). Phosphordiamidic acid (D) is then converted to a salt by treatment with a base.

In certain embodiments, the present invention provides a method for the preparation of a compound of formula (B):

comprising treating a compound of formula (A):

with an alcohol $R^1$—OH under condensation conditions, wherein, as valence and stability permit, $X^1$ independently for each occurrence, is selected from Cl, I, and Br, $R^1$ is benzyl, optionally substituted with one or more substituents, e.g., selected from halogen, —$R^2$, —$OR^2$ and —$NR^2_2$, wherein $R^2$ is independently selected for each occurrence from H and lower alkyl.

In certain embodiments, $R^1$ is benzyl optionally substituted with one or more substituents. In certain embodiments, $R^1$ is unsubstituted benzyl. In certain embodiments, $X^1$ at each occurrence is independently selected from any of —Cl, —Br and —I. In certain embodiments, the compound of formula (A) is $P(O)Cl_3$ and/or $R^1OH$ is $PhCH_2OH$.

In certain aspects, the condensation conditions comprise an amine base. In certain such embodiments, the amine base is selected from any of N-methyl morpholine, triethylamine, pyridine or diisopropylethylamine, e.g., triethylamine.

In certain embodiments, the condensation conditions may comprise an aprotic organic solvent, e.g., acetone, 2-butanone, butyl acetate, ethyl acetate, acetonitrile, toluene, THF, dioxane, N,N-DMF, DMSO, 1,2-dichloroethane, or methylene chloride. In certain embodiments, the aprotic organic solvent comprises acetonitrile, wherein the acetonitrile may represent, for example, more than about 10, 20, 30, 50, 70, or 90% of the solvent system, or substantially all of the solvent system, for example about 95% or greater of the solvent system.

In some embodiments, phosphine oxide A and $R^1OH$ are combined under condensation conditions, e.g., in a ratio in the range of 2:1 to 1:1.2 of compound of formula (A) to $R^1OH$, such as in a ratio in the range of 1.2:1 to 1:1.2, preferably approximately equimolar amounts of the compound of formula (A) and alcohol $R^1OH$.

In certain embodiments, the condensation conditions comprise maintaining a reduced temperature, e.g., in the range of about −50 to about −10° C., such as from about −35 to about −25° C., e.g., about −30° C.

In certain embodiments, the present invention provides a method for the preparation of a compound of formula (C):

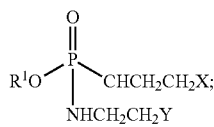

(C)

comprising treating a compound of formula (B):

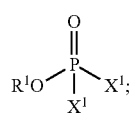

(B)

with amines $XCH_2CH_2NH_2$ and $YCH_2CH_2NH_2$ or salts thereof under condensation conditions, wherein, as valence and stability permit, X and Y independently represent leaving groups which may be the same or different; and $R^1$ is benzyl optionally substituted with one or more substituents, e.g., selected from halogen, —$R^2$, —$OR^2$ and —$NR^2_2$, wherein $R^2$ is independently selected for each occurrence from H and lower alkyl.

In certain embodiments, $R^1$ is benzyl optionally substituted with one or more substituents. In certain embodiments, $R^1$ is unsubstituted benzyl. In certain embodiments, $X^1$ at each occurrence is independently selected from any of Cl, Br and I. In certain embodiments, $R^1$ is unsubstituted benzyl and/or $X^1$ is selected at each occurrence from Cl or Br.

X and Y of amines $XCH_2CH_2NH_2$ and $YCH_2CH_2NH_2$ may be independently selected from halogen, e.g., Cl, Br, or I, or a sulfonate, e.g., toluenesulfonate, methanesulfonate, 2,4,6-triisopropylbenzenesulfonate, or 2,4,6-trimethylbenzenesulfonate. In certain embodiments, X and Y are independently selected from Cl, Br or I. In certain embodiments, X and Y are identical, e.g., X and Y are both Cl. In any of the embodiments of the present disclosure, $XCH_2CH_2NH_2$ and $YCH_2CH_2NH_2$ may be employed in the form of salts such as the HCl salt.

The amine or amines may be introduced to the compound of formula (B) in a single dose, in portions over time, or in multiple smaller doses. In certain embodiments, the amine is steadily added to the compound of formula (B) over a period of time, e.g., with a continuous feed, a syringe pump or an addition funnel.

In embodiments where X and Y of amines $XCH_2CH_2NH_2$ and $YCH_2CH_2NH_2$ are different from one another, e.g., X is Cl and Y is Br, or X is Br and Y is I, the amines, e.g., $ClCH_2CH_2NH_2$ and $BrCH_2CH_2NH_2$, can be introduced to a compound of formula (B) in concert or, preferably, in series. In an example of a serial addition, the amine $ClCH_2CH_2NH_2$ is introduced to the compound of formula (B) in one dose and, e.g., after reacting to completion, amine $BrCH_2CH_2NH_2$ is added.

In certain embodiments, the sum of molar equivalents of amines $XCH_2CH_2NH_2$ and $YCH_2CH_2NH_2$ relative to the compound of formula (B) is a ratio in the range of 2.5:1 to 1.8:1. In certain embodiments, wherein X and Y are leaving groups with the same molecular formula, such that $XCH_2CH_2NH_2$ and $YCH_2CH_2NH_2$ are compounds of the same formula, the ratio of amine components to the compound of formula (B) is approximately 2:1. In certain embodiments, wherein X and Y are not identical substituents, amines $XCH_2CH_2NH_2$ and $YCH_2CH_2NH_2$ are approximately equimolar to each other, and together are added in a ratio of approximately 2:1 relative to the compound of formula (B).

The condensation conditions may comprise an amine base such as N-methyl morpholine, triethylamine, pyridine or diisopropylethylamine. In certain embodiments, the amine base is in a ratio of 5:1 to 3:1 relative to the compound of formula (B). In certain embodiments, the amine base is in a ratio of approximately 4:1 relative to the compound of formula (B). The amine base may be triethylamine in a ratio of 4:1 relative to the compound of formula (B). It will be recognized by those of skill in the art that more amine base will be advantageous when amines $XCH_2CH_2NH_2$ and $YCH_2CH_2NH_2$ are added in their salt form than if they are added in their free-base form. Specifically, the condensation reaction will be facilitated by the addition of two or more equivalents of amine base when $XCH_2CH_2NH_2$ and $YCH_2CH_2NH_2$ are used in their free-base form, whereas four or more equivalents of amine base are preferred when $XCH_2CH_2NH_2$ and $YCH_2CH_2NH_2$ are added as amine salts.

In certain embodiments, the present invention provides a method for the preparation of a compound of formula (C):

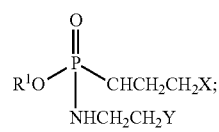

(C)

comprising a. treating a compound of formula (A):

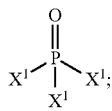

(A)

with an alcohol $R^1$—OH in a reaction mixture under condensation conditions to generate a compound of formula (B):

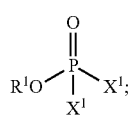

(B)

and b. adding to the reaction mixture amines $XCH_2CH_2NH_2$ and $YCH_2CH_2NH_2$ or a salt or salts thereof under condensation conditions, wherein, independently for each occurrence and as valence and stability permit, X and Y independently represent leaving groups;

$X^1$, independently for each occurrence, is selected from Cl, I, and Br, $R^1$ is benzyl optionally substituted with one or more substituents, e.g., selected from halogen, $-R^2$, $-OR^2$ and $-NR^2{}_2$, wherein $R^2$ is independently selected for each occurrence from H and lower alkyl.

In certain embodiments, $R^1$ is benzyl optionally substituted with one or more substituents. In certain embodiments, $R^1$ is unsubstituted benzyl. In certain embodiments, $X^1$ at each occurrence is independently selected from any of Cl, Br and I. In certain embodiments, $R^1$ is unsubstituted benzyl and/or $X^1$ is selected at each occurrence from Cl or Br, e.g., the compound of formula (A) may be $P(O)Cl_3$.

In certain aspects, the condensation conditions comprise an amine base. In certain such embodiments, the amine base is selected from any of N-methyl morpholine, triethylamine, pyridine or diisopropylethylamine, e.g., triethylamine.

The condensation conditions may comprise an aprotic organic solvent, e.g., one or more of acetone, 2-butanone, butyl acetate, ethyl acetate, acetonitrile, toluene, THF, dioxane, N,N-DMF, DMSO, 1,2-dichloroethane, or methylene chloride. In certain embodiments, the aprotic solvent comprises acetonitrile, wherein the acetonitrile may represent, for example, more than about 10, 20, 30, 50, 70, or 90% of the solvent system, or substantially all of the solvent system, for example about 95% or greater of the solvent system.

In some embodiments, phosphine oxide (A) and $R^1$OH are combined under condensation conditions, e.g., in a ratio in the range of 2:1 to 1:1.2 of compound of formula (A) to $R^1$OH, such as in a ratio in the range of 1.2:1 to 1:1.2, e.g., in approximately equimolar amounts of the compound of formula (A) and substitution reagent $R^1$OH.

In certain embodiments, the condensation conditions comprise maintaining an reduced temperature, e.g., in the range of about −50 to about −10° C., or from about −35 to about −25° C., or about −30° C.

X and Y of amines $XCH_2CH_2NH_2$ and $YCH_2CH_2NH_2$ may be independently selected from halogen, e.g., Cl, Br, or I or a sulfonate, e.g., toluenesulfonate, methanesulfonate, 2,4,6-triisopropylbenzenesulfonate, or 2,4,6-trimethylbenzenesulfonate. In certain embodiments, X and Y are independently selected from Cl, Br or I. In certain embodiments, X and Y are identical, e.g., both Cl. In any of the embodiments of the present disclosure, $XCH_2CH_2NH_2$ and $YCH_2CH_2NH_2$ may be employed in the form of salts, such as the HCl salt.

The amine may be introduced to the reaction mixture in a one-time dose, in portions over time, or in multiple smaller doses. In certain embodiments, the amine is steadily added to the compound of formula (B) over a period of time, e.g., with a syringe pump, an addition funnel, or continuous feed.

In embodiments wherein X and Y of amines $XCH_2CH_2NH_2$ and $YCH_2CH_2NH_2$ are distinct from one another, e.g., X is Cl and Y is Br, or X is Br and Y is I, the amines, e.g., $ClCH_2CH_2NH_2$ and $BrCH_2CH_2NH_2$, may be introduced to the reaction mixture in concert or, preferably, in series. In an example of a serial addition, the amine $ClCH_2CH_2NH_2$ is introduced to the reaction mixture in one dose and, e.g., after reacting to completion, amine $BrCH_2CH_2NH_2$ is added.

In certain embodiments, the sum of molar equivalents of amines $XCH_2CH_2NH_2$ and $YCH_2CH_2NH_2$ relative to the compound of formula (A) are in a ratio in the range of 2.5:1 to 1.8:1. In certain embodiments, wherein X and Y are leaving groups with the same molecular formula, such that $XCH_2CH_2NH_2$ and $YCH_2CH_2NH_2$ are compounds of the same formula, the ratio of amine components to the compound of formula (A) is approximately 2:1. In certain embodiments, wherein X and Y are not identical substituents, amines $XCH_2CH_2NH_2$ and $YCH_2CH_2NH_2$ are approximately equimolar to each other, and together are added in a ratio of approximately 2:1 relative to compound of formula (A).

The condensation conditions may comprise an amine base such as N-methyl morpholine, triethylamine, pyridine or diisopropylethylamine. In certain embodiments, the amine base is in a ratio of 5:1 to 3:1 relative to the compound of formula (A). In certain embodiments, the amine base is in a ratio of approximately 4:1 relative to the compound of formula (A). The amine base may be triethylamine in a ratio of 4:1 relative to the compound of formula (A). It will be recognized by those of skill in the art that more amine base will be advantageous when amines $XCH_2CH_2NH_2$ and $YCH_2CH_2NH_2$ are added in their salt form than if they are added in their free-base form. Specifically, the condensation reaction will be facilitated by the addition of two or more equivalents of amine base when $XCH_2CH_2NH_2$ and $YCH_2CH_2NH_2$ are used in their free-base form, whereas four or more equivalents of amine base are preferred when $XCH_2CH_2NH_2$ and $YCH_2CH_2NH_2$ are added as amine salts (in addition to any amine base used in the condensation with alcohol $R^1$OH, e.g., typically at least one further equivalent).

In certain embodiments the reaction mixture comprising the product of the reaction of the compound of formula (B) to form the compound of formula (C) is used in the hydrogenolysis reaction, e.g., without first purifying or partially or completely removing solvents from the reaction mixture. For example, the reaction mixture may be filtered to remove solids, e.g., salt by-products of the condensation conditions, prior to subjecting the solution to the hydrogenolysis conditions affording the compound of formula (D). The reaction mixture may be filtered by any method known in the art to remove solids from the solvent of the reaction mixture. In some embodiments, the reaction mixture is filtered and substantially directly subjected to hydrogenation conditions, e.g., the compound of formula (C) is not further purified or isolated from the reaction mixture (e.g., no extractions, chromatography, or quenches are performed).

In certain embodiments, the present invention provides a method for the preparation of a compound of formula (D):

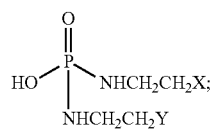

(D)

comprising treating a compound of formula (C):

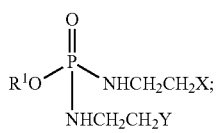

(C)

with a reducing agent under hydrogenolysis conditions, wherein, as valence and stability permit, X and Y independently represent leaving groups; and $R^1$ is benzyl optionally substituted with one or more substituents, e.g., selected from halogen, $-R^2$, $-OR^2$ and $-NR^2{}_2$, wherein $R^2$ is independently selected for each occurrence from H and lower alkyl.

In certain embodiments, $R^1$ is benzyl optionally substituted with one or more substituents. In certain embodiments, $R^1$ is unsubstituted benzyl. In certain embodiments, X and Y at each occurrence are independently selected from halogens such as Cl, Br and I. In certain embodiments, $R^1$ is unsubstituted benzyl and/or X and Y are both Cl.

In certain embodiments the reaction mixture comprising the product of the reaction of the compound of formula (B) to form the compound of formula (C) is used in the hydrogenolysis reaction, e.g., without first purifying or partially or completely removing solvents from the reaction mixture. For example, the reaction mixture may be filtered to remove solids, e.g., salt by-products of the condensation conditions, prior to subjecting the solution to the hydrogenolysis conditions affording the compound of formula (D). The reaction mixture may be filtered by any method known in the art to remove solids from the solvent of the reaction mixture. In some embodiments, the reaction mixture is filtered and substantially directly subjected to hydrogenation conditions, e.g., the compound of formula (C) is not further purified or isolated from the reaction mixture (e.g., no extractions, chromatography or quenches are performed).

The hydrogenolysis conditions may comprise treating the compound of formula (C) with hydrogen gas in the presence of a catalyst. The catalyst may be selected from any suitable hydrogenolysis catalyst, such as Pd/carbon, Pd black, Pd EnCat (polymer encapsulated active metal catalyst) Raney nickel, Rh/carbon, Ru/carbon, Re/carbon, palladium oxide, palladium chloride, $PtO_2$ or $RuO_2$. In certain embodiments, the hydrogenolysis catalyst comprises palladium, e.g., Pd/carbon.

In certain embodiments, the hydrogenolysis conditions comprise a partial pressure of hydrogen greater than 1 atmosphere. In certain embodiments, the partial pressure of hydrogen is less than or equal to 100, 75 or 50 psi. In certain embodiments, the partial pressure of hydrogen is selected from between 10 psi and 50 psi. The partial pressure of hydrogen may be from 20-50 psi, such as from 40-50 psi. Alternatively, the partial pressure of hydrogen during hydrogenolysis may be about 50 psi, or even between 50 and 75 psi.

In certain embodiments, the hydrogenolysis conditions may comprise an aprotic organic solvent, e.g., toluene, xylene, benzene, furan, acetonitrile, dioxane, tetrahydrofuran, chloroform or mixtures thereof. In certain embodiments, the aprotic solvent comprises acetonitrile, wherein the acetonitrile may represent, for example, more than about 10, 20, 30, 50, 70, or 90% of the solvent system, or substantially all of the solvent system, for example about 95% or greater of the solvent system.

In certain embodiments, the separation of the product from residual catalyst is achieved by the formation of a basic salt under aqueous conditions, e.g., using sodium hydroxide or another base in water, which may be performed in situ. The resulting salt may be dissolved in a suitable solvent and the residual catalyst may be filtered to remove solids from the solvent of the reaction mixture.

In certain embodiments, the separation of the product from residual catalyst is achieved by the formation of a basic salt under anhydrous conditions, e.g., using triethylamine or another base, e.g., an amine base, preferably a sterically hindered base such as diisopropylethylamine or proton sponge. The subsequent salt may be dissolved into the reaction solvent and the residual catalyst may be filtered to remove solids from the solvent of the reaction mixture.

In certain embodiments, the present invention provides a method for the preparation of a compound of formula (E):

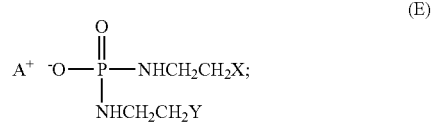

(E)

comprising treating a compound of formula (D):

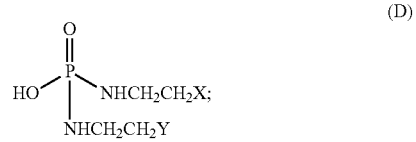

(D)

with a base under salt-forming conditions, wherein as valence and stability permit, X and Y independently represent leaving groups; and $A^+$ represents an ammonium cation.

In certain embodiments, X and Y at each occurrence are independently selected from halogens such as —Cl, —Br and —I. In certain embodiments, X and Y are both Cl.

In certain embodiments, $A^+$ represents $BH^+$ and B is an amine selected from the basic amino acids, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. In certain embodiments, B is tris(hydroxymethyl)methylamine.

In certain embodiments, the salt-forming conditions comprise combining approximately equimolar amounts of an amine base and the compound of formula (D). In certain embodiments the compound of formula (D) and the amine base are combined in a molar ratio in the range of 1:1 to 1:10. In certain embodiments, the salt-forming conditions comprise combining approximately equimolar amounts of tris(hydroxymethyl)aminomethane and the compound of formula (D).

In certain embodiments, the salt-forming conditions comprise a polar aprotic solvent, such as N,N-DMF, acetone, DMSO, THF, 2-butanone, butyl acetate, ethyl acetate, acetonitrile, and combinations thereof. In certain embodiments, the aprotic solvent comprises N,N-DMF, wherein the N,N-DMF may represent, for example, more than about 10, 20, 30, 50, 70, or 90% of the solvent system, or substantially all of the solvent system, for example about 95% or greater of the solvent system.

In certain embodiments, the invention relates to a compound comprising a crystalline salt of IPM or analog thereof wherein the IPM or analog thereof, and the counterion, preferably tris(hydroxymethyl) amino methane (tris), are present in a ratio from 2:1 to 1:2, preferably 1:1. In certain embodiments, the crystalline formulation comprises more than one polymorphic form of crystals, such as two, three, four, or even five polymorphic forms of crystals. In certain alternative such embodiments, the crystalline formulation comprises a single polymorphic form of crystals. In certain embodiments, such salts are more stable than IPM and IPM analogs as free acids.

In certain such embodiments, the compound is a crystalline salt of a 1:1 ratio of IPM and Tris. In certain such embodiments, the melting point of the crystalline solid is between about 100 and about 110° C., about 102 to about 108° C., about 103 to about 106° C., or even 105 to 106° C.

In certain embodiments, the compound, e.g., a crystalline salt of a 1:1 ratio of IPM and Tris, is at least about 80% pure, at least about 85% pure, at least 90% pure, at least 95% pure, at least 97% pure, at least 98% pure, or even at least 99% pure. In certain such embodiments, no single impurity exceeds 1% by weight. In certain embodiments, purity is measured relative to all other components of the formulation, while in other embodiments (e.g., where the compound is part of a pharmaceutical formulation or lyophilisate mixture), purity may be measured relative to degradation products of the compound (e.g., phosphorous-containing degradation products of the compound) or by-products of the manufacture of the compound (e.g., phosphorous-containing degradation products of the compound), thereby excluding other components purposefully added to the formulation.

EXEMPLIFICATION

The foregoing disclosure is further explained by the following non-limiting examples.

Examples

Example 4

This example describes the evaluation of IPM against several different cancer cell lines implanted in mice. The mice tolerated intraperitoneal (IP) and intravenous (IV) treatment with IPM well in each study; the only toxicities are organ pathologies observed at autopsy that were associated with the induced tumors.

First, IPM was evaluated against two L1210 variants, L1210/0 and L1210/CPA cell lines implanted in mice, as compared with Ifos. The dosages for IPM were 50% of the dose for Ifos. ILS was observed for all three agents in the L1210/0 treated groups. However, for the L1210/CPA model, the IPM treatment demonstrated superiority over the other two arms (Ifos vs CPA). In the CPA resistant tumor line, the IPM treated animals had a two-fold increase in survival with a tumor burden reduction of 7. For the L1210/0 tumor model, IPM was equally active to CPA and Ifos, but at a lower dose. This demonstrates that CPA resistant cells are not cross-resistant to IPM. The results of this study are recorded below in Table 2a.

TABLE 2a

Activity of isophosphoramide mustard against L1210/0 and L1210/CPA leukaemias
(Optimal response at #LD$_{10}$ dose, from dose-response study)

| | | L1210/0† Tumor burden at start of $R_x = 8.5 \times 10^7$ cells | | | L1210/CPA† Tumor burden at start of $R_x = 6.0 \times 10^7$ cells | | |
|---|---|---|---|---|---|---|---|
| Agent | Dosage* (mg kg$^{-1}$) | Day 60 Survivors/ total | % ILS (dying mice only) | Net log$_{10}$ Reduction in tumor burden after therapy‡ | Day 60 survivors/ total | % ILS (dying mice only) | Net log$_{10}$ Reduction in tumor burden after therapy‡ |
| Cyclophosphamide | 200 | 0/10 | +107 | 7 | 0/10 | +57 | 4 |
| Ifosfamide | 431 | 0/10 | +185 | 8 | 0/10 | +85 | 5 |
| | 289 | 0/9 | +114 | 8 | 0/10 | +57 | 4 |
| Isophosphoramide mustard | 100 | 0/10 | +128 | 8 | 1/10 | +114 | 7 |

*Treatment: IP; day 2 only; highest non-toxic dose (LD$_{10}$ or less) in a range of doses.
†IP; 10$^6$ cells, in male CDF$_1$ mice.

A second study demonstrates the inhibition of Lewis lung carcinoma by IPM in mice implanted with Lewis lung carcinoma tumors. Single second day IP dosings with CPA, Ifos, PM and IPM to mice bearing Lewis lung carcinoma revealed that IPM yielded 6/10 tumor free survivors, as compared to 7/10 for Ifos and 5/10 for CPA at equitoxic, equal doses. The single dose schedule was used for each agent and the activities noted (T-C) were the same between all four agents.

The results of this study, recorded in Table 3a, demonstrate that IPM is effective against Lewis lung carcinoma.

TABLE 3a

Response of Lewis Lung Carcinoma to Isophosphoramide Mustard Implant
Size: 20-30 mg; Implant Site: s.c.; Drug Treatment: IP

| Agent | Schedule | Highest non-toxic dosage (mg kg$^{-1}$/dose) | Tumor-free survivors | T − C*† | % ILS ‡ | Log kill totalδ |
|---|---|---|---|---|---|---|
| Cylophosphamide | Day 2 Single dose | 200 | 5/10 | 27 | 68 | >6.8 |
| Ifosfamide | Day 2 Single dose | 300 | 7/10 | 18 | 55 | >4.5 |
| Phosphoramide mustard | Day 2 Single dose | 200 | 0/10 | 4.9 | 15 | 1.2 |
|  | Day 2 Q5 min x 7 | 30 | 0/10 | 6.1 | 17 | 1.5 |
| Isophosphoramide mustard | Day 2 Single dose | 100 | 6/10 | 8.4 | 34 | >2.1 |

*Tumor growth delay (T − C), where T = median time (days) required for the treatment-group tumors and C, the control group tumors (median of 120 each) to reach a predetermined weight (750 mg). Tumor-free survivors were excluded from these calculations.
†Control: Median day of death = 29; time for median tumor to reach 750 mg = 10.4 days; there were no tumor-free survivors among the 30 control mice.
‡ Increase in life span, excluding survivors.
δThe Log$_{10}$ cell kill (total) was calculated from the following formula: Log kill = T − C value/(3.32 T$_4$). Where T$_4$ is the tumor volume-doubling time measured from a best fit straight line of the control-group tumors in exponential growth (100-400 mg range). T$_4$ = 1.2 for Lewis tumor in this experiment.

A third study evaluated the efficacy of IPM in the inhibition of B16 melanoma growth. Single dose administrations of IPM at 150 mg revealed that IPM was slightly inferior to CPA but better than Ifos in this resistant animal model. There were no statistical differences between % ILS responses between the three therapeutic agents. The results of this study, recorded in Table 4a, demonstrate the efficacy of IPM against melanoma.

TABLE 4a

A Comparison of the Response of s.c. B16 Melanoma to Cyclophosphamide, Isophosphoramide Mustard, Phosphoramide Mustard, and Ifosfamide

| Agent | Rx Schedule | Dosage (mg mg$^{-1}$) | Tumor-free survivors | T-C* (days) | % ILS |
|---|---|---|---|---|---|
| Cylophosphamide | Day 2 Single dose | 200 | 5/10 | 27 | 68 |
| Ifosfamide | Day 2 Single dose | 300 | 7/10 | 18 | 55 |
| Phosphoramide mustard | Day 2 Single dose | 200 | 0/10 | 4.9 | 15 |
|  | Day 2 Q5 min × 7 | 30 | 0/10 | 6.1 | 17 |
| Isophosphoramide mustard | Day 2 Single dose | 100 | 6/10 | 8.4 | 34 |

*See footnote with Table 3a, above. Predetermined weight was 750 mg.

A fourth study evaluated IPM in the inhibition of P388 Leukemia in mice. In this animal model, IPM was comparably effective to CPA and Ifos against IP implanted P388 leukemia as indicated by >log$_{10}$ cell kill, although it produced fewer tumor-free survivors. However, with the P388/CPA tumor model, there was significantly improved cell kill as well as % ILS for IPM as compared to CPA and Ifos. The results of this study are recorded in Table 5a. All data is statistically significant and demonstrates that IPM can be used against CPA resistant or treated tumors as well as for patients pretreated with other agents.

TABLE 5a

Activity of isophosphoramide mustard against P388/0 and P388/CPA leukaemias
(Optimal response at #LD$_{10}$ dose, from dose-response study)

| | | P388/0† Tumor burden at start of R$_x$ = ~4.4 × 10$^6$ cells | | | P388/CPA† Tumor burden at start of R$_x$ = ~4.6 × 10$^6$ cells | | |
|---|---|---|---|---|---|---|---|
| Agent | Dosage* (mg kg$^{-1}$) | Day 60 survivors/ total | % ILS (dying mice only) | Net log$_{10}$ reduction in tumor burden after therapy‡ | Day 60 survivors/ total | % ILS (dying mice only) | Net log$_{10}$ Reduction in tumor burden after therapy‡ |
| CPA | 265 | 7/10 | +280 | 7 | 0/10 | +35 | 3 |
|  | 175 | 4/10 | +130 | 7 | 0/10 | +35 | 3 |
| Ifos | 538 | 7/10 | +210 | 7 | 0/10 | +42 | 4 |
|  | 431 | 7/10 | +130 | 7 | 0/10 | +39 | 4 |
| IPM | 125 | 0/9 | +100 | 6 | 0/10 | +71 | 7 |
|  | 100 | 1/10 | +140 | 7 | 0/10 | +85 | 7 |

*Treatment: IP; day 1 only; highest non-toxic dose (LD$_{10}$ or less) in a range of doses.
†Implant: IP; 10$^6$ cells, in female CDF$_1$ mice.

A fifth study evaluated the inhibition of implanted M5076 sarcoma with IPM in mice. IPM in doses of 18-40 mg/kg were injected IP to growing tumors daily for five days (the compound was injected IP daily on days 11-15). T-C was 6.1 days at 40 mg/kg. The doses were tolerated well with significant improvement in response. The mice tolerated the IP treatments well; the only toxicities are organ pathologies observed at autopsy that were associated with the induced tumors. The results of this study, recorded in Table 6a, demonstrate that IPM is effective against sarcoma in a dose-dependent fashion.

TABLE 6a

Response of SC Implanted M5076 Sarcoma to Treatment with IPM

| Agent | Dose (mg/kg) | Days To 2 doublings | Days Delay (T-C) |
|---|---|---|---|
| IPM | 40 | 15.4 | 6.1 |
| IPM | 27 | 12.6 | 3.3 |
| IPM | 18 | 10.3 | 1 |

A sixth study evaluated the inhibition of implanted 16/C mammary tumors in mice. Mice were implanted with the 16/C mammary tumor, and when the tumors were palpable/measurable, were treated with CPA, Ifos and IPM, as individual agents. CPA and Ifos were used as controls for IPM. The drugs were administered IP in doses of 30-60 mg/kg/per day for 4 days, starting on day 7 after tumor implantation. There was statistical improvement in activity for IPM as compared to CPA and Ifos, at all doses for the three agents. IPM was superior in 'days to 2 doublings' and 'days delay (T-C)' when compared to Ifos and CPA at the same dosage/day against this aggressive murine mammary tumor. All ratios were within confidence limits. This data (recorded in Table 7a) demonstrates the efficacy of IPM against mammary tumors and the four day dosings further support the superiority of multiple dosings for IPM.

TABLE 7a

Response of SC 16/C Mammary Tumor to Treatment with CPA, IFOS, and IPM

| Agent | Dose (mg/kg) | Route | Schedule | | Days to 2 Doublings | Days Delay (T − C) |
|---|---|---|---|---|---|---|
| Control | | IP | Q 1dx 4 day 7 | CONTROL | 3.2 | |
| CPA | 60 | IP | Q 1dx 4 day 7 | CPA | 7.7 | 4.5 |
| CPA | 50 | IP | Q 1dx 4 day 7 | | 7.2 | 4.0 |
| CPA | 40 | IP | Q 1dx 4 day 7 | | 4.4 | 1.2 |
| CPA | 30 | IP | Q 1dx 4 day 7 | | 3.6 | 0.4 |
| IFOS | 60 | IP | Q 1dx 4 day 7 | IFOS | 4.6 | 1.4 |
| IFOS | 50 | IP | Q 1dx 4 day 7 | | 4.9 | 1.7 |
| IFOS | 40 | IP | Q 1dx 4 day 7 | | 3.8 | 0.6 |
| IFOS | 30 | IP | Q 1dx 4 day 7 | | 4.0 | 0.8 |
| IPM | 50 | IP | Q 1dx 4 day 7 | IPM | 9.5 | 6.3 |
| IPM | 40 | IP | Q 1dx 4 day 7 | | 8.5 | 5.2 |
| IPM | 30 | IP | Q 1dx 4 day 7 | | 7.4 | 4.2 |

A seventh study evaluated IPM against IP implanted human lox-IMVI melanoma. Nude mice were implanted IP with the human Lox melanoma and treated for five days with either CPA or IPM. Doses for both were 40 mg/kg daily IV×5 days. % ILS was +121 for CPA and +52 IPM. However, excellent responses were seen and doses were well tolerated. Responses were within confidence levels. The results of this study (recorded in Table 8a) demonstrate the efficacy of IV administration of IPM and further demonstrate the efficacy of IPM against human melanoma.

TABLE 8a

| Treatment: IV; Q1DX5 (1) | | Therapeutic Response | |
|---|---|---|---|
| Agent | Dosage (mg/kg/dose) | Median Day of Death | % ILS |
| Control | — | 19.0 | — |
| CPA | 40 | 42.0 | +121 |
| IPM | 40 | 29.0 | +52 |

An eighth study evaluated the inhibition of human MX-1 mammary tumors with IPM. Daily IP administration of CPA, Ifos or IPM was compared in 40-60 mg/kg dosing on a schedule of daily×5 days beginning with day 12 (after implantation). The data recorded in Table 9a demonstrates that IPM is active against human mammary tumors. All ratios were in confidence limits.

TABLE 9a

Response of SC MX-1 Mammary Tumor to Treatment with CPA, IFOS, and IPM

| Agent | Dose (mg/kg) | Route | Schedule | Days to 2 doublings | Days Delay (T-C) |
|---|---|---|---|---|---|
| CPA | 60 | IP | Q 1d × 5 day 12 | >48.0 | >40.5 |
| IFOS | 60 | IP | Q 1d × 5 day 12 | 39.4 | 31.9 |
| IFOS | 40 | IP | Q 1d × 5 day 12 | 16.1 | 8.6 |
| IPM | 60 | IP | Q 1d × 5 day 12 | 26.5 | 19.0 |
| IPM | 40 | IP | Q 1d × 5 day 12 | 14.2 | 6.7 |

Example 5

This example compares the efficacy of IPM and that of IPM.(LYS)$_2$ and IPM.(NH$_4$)$_2$ salt against various hyperproliferative cell lines.

The efficacy of IPM and IPM.(LYS)$_2$ salt and IPM.(NH$_4$)$_2$ salt against Lewis lung murine tumor was compared when the compounds were administered by IP routes daily for 5-days in doses of 20-125 mg/kg daily×5 days, beginning with day 6 (after implantation). IPM and its lysine salt possessed equivalent activities at doses that reflected a 2-fold increase for the MTD (mg/kg/dose) of the salt over parent drug. All ratios were within confidence limits. The mice tolerated IP administration of the salt well; the only toxicities are organ pathologies observed at autopsy that were associated with the induced tumors. The results of this study (recorded in Table 10a) demonstrate that IPM.(LYS)$_2$ exhibits equivalent efficacy to IPM against Lewis lung murine tumor, and that the IPM.(NH$_4$)$_2$ salt is effective against Lewis lung murine tumor.

TABLE 10a

Lewis Lung Murine Tumors

| Agent | MTD Dosage (mg/kg/dose) | T-C (days) |
|---|---|---|
| IPM lysine salt | 93.2 | 8.3* |
| IPM ammonium salt | 42.8 | 9.1 |
| IPM | 40.0 | 12.5* |

Implant: 20-30 mg tumor fragments
Treatment Route: Intraperitoneal
Schedule: q1d × 5 starting day 6
*Although the T-C values are statistically different (P = 0.004), the antitumor activities are comparable.

A second comparison of the efficacy of IPM, IPM.(LYS)$_2$ salt and IPM.(NH$_4$)$_2$ salt was conducted with respect to inhibition of MX-1 mammary tumors. In this study, the effects of IPM and IPM.(LYS)$_2$ salt were compared when administered IP, in doses of 20-100 mg/kg daily×5 days, beginning with day 12 following implantation of MX-1 mammary tumors in mice. IPM.(LYS)$_2$ salt was 8-fold superior to IPM at comparable dosing. The MTD was also higher for the lysine salt. All ratios were within confidence limits. The mice tolerated the IP treatment with IPM.(LYS)$_2$ and IPM.(NH$_4$)$_2$ salts well; the only toxicities are organ pathologies observed at autopsy that were associated with the induced tumors. This data (recorded in Table 11a) demonstrates that both IPM.(LYS)$_2$ salt and IPM.(NH$_4$)$_2$ salt are significantly superior to IPM against human breast tumor cells.

TABLE 11a

MX-1 Human Breast Tumor

| Agent | MTD Dosage (mg/kg/dose) | T-C (days) |
|---|---|---|
| IPM lysine salt | 93.2 | 10.2* |
| IPM ammonium salt | 28.6 | 4.6 |
| IPM | 40.0 | 2.1* |

Implant: 20-30 mg tumor fragments subcutaneously in the mammary fat pad
Treatment Route: Intraperitoneally
Schedule: q1d × 5 starting day 12
*P-value = 0.041

Example 6

This example describes the evaluation of the acute toxicity of isophosphoramide mustard lysine salt, following three days of daily intravenous (bolus) injection in mice. This study consisted of two phases.

First, the dose range-finding phase consisted of four treatment groups (one mouse/sex/group) that received the test article as a single daily dose for three consecutive days at respective dose levels of 100, 200, 400, and 600 mg/kg. The vehicle was 0.9% sodium chloride for injection, USP and all doses were at a constant volume of 15 mL/kg. The animals were observed for seven days following dosing. On Day 10, following the seven-day observation period, all surviving dose range-finding phases are presented. Based on the deaths noted in the dose range-finding phase at 200, 400, and 600 mg/kg, the dose levels chosen for the main study phase were 50, 75, 100, 200, 300, 500, and 600 mg/kg (see below).

The second main study phase consisted of eight treatment groups (five mice/sex/group) that received the test article as a single daily dose for three consecutive days at respective dose levels of 50, 75, 100, 200, 300, 400, 500, and 600 mg/kg. An additional group (5 mice/sex) served as a parent compound control and received the isophosphoramide mustard parent compound in the same manner, at a dose level of 150 mg/kg. The vehicle was 0.9% sodium chloride for injection, USP and all doses were at a constant volume of 15 mL/kg. The animals were observed for 11 days following the three-day dosing period.

Observations for mortality, morbidity, and the availability of food and water were conducted twice daily for all animals. Observations for clinical signs were conducted daily during the study (approximately one and four hours postdose on Days 1, 2, and 3, and once daily on non-dosing days). Body weights for all surviving animals were measured and recorded the second day after receipt, prior to randomization, and on Days −1 and 7. Body weights also were measured on all surviving main study phase animals on Day 14. Macroscopic evaluations were performed on each main study animal at necropsy (Day 15).

Animal Acquisition and Acclimation:

A total of 62 male and 61 female Crl: CD-1(1CR) BR mice (approximately six weeks old) were received from Charles River Laboratories, Portage, Mich., on Apr. 21, 2003. During the seven- to 16-day acclimation period, the sex of the animals was verified, the animals were weighed and observed twice daily with respect to general health and any signs of disease. At receipt, the animals were housed three to four mice/cage in order to acclimate to the automatic watering system. Three days after receipt, the animals were housed individually. All animals were given a detailed clinical observation prior to selection for study.

Randomization, Assignment to Study, and Maintenance:

Prior to assignment to study, the mice were weighed and examined for evidence of disease and other physical abnormalities. Animals assigned to the study had body weights within 20% of the mean body weight for each sex. Using a simple randomization procedure, the animals were placed into the treatment groups. Extra animals obtained for this study were euthanized via carbon dioxide inhalation and discarded.

Forty-nine male and 49 female mice (weighing 24.8 to 29.1 g and 21.5 to 24.2 g, respectively, at randomization) were assigned to the treatment groups identified in Table 12a.

Each animal was assigned an animal number to be used in Provantis™ and was implanted with a microchip bearing a unique identification number. The individual animal number, implant number, and study number comprised a unique identification for each animal. The cage was identified by the animal number, study number, group number, and sex. Animal identification was verified during the course of the study as documented in the data.

The animals were individually housed in suspended, stainless steel, wire-mesh type cages. Fluorescent lighting was provided for approximately 12 hours per day and controlled via an automatic timer. Temperature and humidity were monitored and recorded daily, and maintained between 68 to 74° F. and 30 to 68%, respectively.

The dose levels for the dose range-finding phase were selected on the basis of available data from previous studies. The dose levels for the main study phase were set following a review of the results from the dose range-finding phase, with the exception of the 150 mg/kg parent compound control group, whose dose level was selected on the basis of available data from previous studies.

TABLE 12a

Group Assignments

| Group Number | Dose Level (mg/kg) | Number of Animals | |
|---|---|---|---|
| | | Male | Female |
| Dose Range-finding Phase$^a$ | | | |
| 1 | 100 | 1 | 1 |
| 2 | 200 | 1 | 1 |
| 3 | 400 | 1 | 1 |
| 4 | 600 | 1 | 1 |
| Main Study Phase$^b$ | | | |
| 5$^c$ | 150 | 5 | 5 |
| 6 | 50 | 5 | 5 |
| 7 | 75 | 5 | 5 |
| 8 | 100 | 5 | 5 |
| 9 | 200 | 5 | 5 |

TABLE 12a-continued

| Group Assignments | | | |
|---|---|---|---|
| Group Number | Dose Level (mg/kg) | Number of Animals | |
| | | Male | Female |
| 10 | 300 | 5 | 5 |
| 11 | 400 | 5 | 5 |
| 12 | 500 | 5 | 5 |
| 13 | 600 | 5 | 5 |

[a]Animals were dosed for three days, followed by a seven-day observation period.
[b]Animals were dosed for three days, followed by a 11-day observation period.
[c]This group was dosed with Isophosphoramide Mustard Parent Compound (Parent Compound Control).

Administration:

Four range-finding treatment groups (one mouse/sex/group) received the test article as a single daily dose for three consecutive days via intravenous (bolus) injection at respective dose levels of 100, 200, 400, and 600 mg/kg. All doses were at a volume of 15 mL/kg and based on the most recent body weights.

Eight main study treatment groups received the test article as a single daily dose for three consecutive days via intravenous (bolus) injection at respective dose levels of 50, 75, 100, 200, 300, 400, 500, and 600 mg/kg. An additional group (five mice/sex) served as a parent compound control and received the Isophosphoramide Mustard Parent Compound in the same manner at a dose level of 150 mg/kg. All doses were at a volume of 15 mL/kg and based on the most recent body weight.

While the animal was restrained, the dosing formulation was administered through a needle that was inserted into the tail vein and the hub of the needle was observed for the presence of blood to ensure the proper placement of the needle in the vein. The dose was then administered at the absolute dose volume for each animal.

Observation and Examination:

All mice were observed for morbidity, mortality, injury, and the availability of food and water twice daily throughout the duration of the study.

A detailed clinical examination of each animal was performed at one and four hours postdose on Days 1, 2, and 3, and once daily on non-dosing days. The observations included, but were not limited to, evaluation of the skin, fur, eyes, ears, nose, oral cavity, thorax, abdomen, external genitalia, limbs and feet, respiratory and circulatory effects, autonomic effects such as salivation, and nervous system effects including tremors, convulsions, reactivity to handling, and bizarre behavior.

Body weights for all surviving animals were measured and recorded the second day after receipt, prior to randomization, and on Days −1 and 7. Body weights also were measured on all surviving main study phase animals on Day 14. The body weights recorded after receipt and prior to randomization are not reported, but are maintained in the study file.

On Day 10, all surviving dose range-finding phase animals were euthanized and discarded. No necropsies were conducted on any dose range-finding animals. All main study animals received a complete necropsy examination under procedures approved by a veterinary pathologist. At the termination of the study, all surviving main study phase animals were euthanized by carbon dioxide inhalation and exsanguination via abdominal vena cava.

Each animal was examined carefully for external abnormalities including masses. The skin was reflected from a ventral midline incision and any subcutaneous abnormalities were identified and correlated with antemortem findings. The abdominal, thoracic, and cranial cavities were examined for abnormalities and the organs were removed and examined. All abnormalities were recorded. No tissues were saved and the carcasses were discarded.

Statistics:

When appropriate, the $LD_{50}$ and the $LD_{10}$ and their 95% confidence limits were calculated using the Probit Procedure (SAS Institute, Inc. SAS/STAT® User's Guide, Version 6, Fourth Edition, Volume 2. Cary N.C.: SAS Institute; 1989) in SAS® (main study treated groups).

The computer systems used during the conduct of this study are presented in Table 13a.

TABLE 13a

| Computer Systems |
|---|
| In-life System: Provantis ™ |
| Randomization: Provantis ™ |
| Pathology: Provantis ™ |
| Statistical Analyses: SAS |
| Reporting: SAS and Microsoft Office Professional |

Results:

The following data are the results of the definitive main study phase.

A summary of mortality results is presented in Table 14a below. The mortality results generally exhibit a typical dose-response effect, with IPM Lysine Salt being slightly more toxic in females than in males. The IPM parent compound control group exhibited the expected mortality, as well as greater toxicity in females than males, correlating with available data from previous studies.

TABLE 14a

Mortality by Day of Study and Cumulatively

| Dose Level (mg/kg) | Study Day (Male/Female) | | | | | | | | | | | | | | | Cumulative Mortality | |
|---|---|---|---|---|---|---|---|---|---|---|---|---|---|---|---|---|---|
| | 1 to 5 | | 6 | | 7 | | 8 | | 9 | | 10 | | 11 | | 12 to 14 | | |
| | M | F | M | F | M | F | M | F | M | F | M | F | M | F | M | F | M F | Total |
| 150[a] | 0 | 0 | 0 | 1 | 0 | 1 | 0 | 2 | 0 | 0 | 0 | 0 | 1 | 0 | 0 | 0 | 1/5 4/5 | 5/10 |
| 50 | 0 | 0 | 0 | 0 | 0 | 0 | 0 | 0 | 0 | 0 | 0 | 0 | 0 | 0 | 0 | 0 | 0/5 0/5 | 0/10 |
| 75 | 0 | 0 | 0 | 0 | 0 | 0 | 0 | 0 | 0 | 0 | 0 | 0 | 0 | 0 | 0 | 0 | 0/5 0/5 | 0/10 |
| 100 | 0 | 0 | 0 | 0 | 0 | 0 | 0 | 0 | 1 | 0 | 0 | 0 | 0 | 0 | 0 | 0 | 1/5 0/5 | 1/10 |
| 200 | 0 | 0 | 0 | 0 | 0 | 0 | 0 | 0 | 0 | 0 | 0 | 2 | 0 | 0 | 0 | 1[b] | 0/5 3/5 | 3/10 |
| 300 | 0 | 0 | 0 | 1 | 1 | 3 | 1 | 0 | 0 | 0 | 1 | 1 | 1 | 0 | 0 | 0 | 4/5 5/5 | 9/10 |

TABLE 14a-continued

Mortality by Day of Study and Cumulatively

| Dose Level (mg/kg) | 1 to 5 | | 6 | | 7 | | 8 | | 9 | | 10 | | 11 | | 12 to 14 | | Cumulative Mortality | | |
|---|---|---|---|---|---|---|---|---|---|---|---|---|---|---|---|---|---|---|---|
| | M | F | M | F | M | F | M | F | M | F | M | F | M | F | M | F | M | F | Total |
| 400 | 0 | 0 | 0 | 4 | 3 | 1 | 1 | 0 | 0 | 0 | 0 | 0 | 1 | 0 | 0 | 0 | 5/5 | 5/5 | 10/10 |
| 500 | 0 | 0 | 4 | 2 | 1 | 3 | 0 | 0 | 0 | 0 | 0 | 0 | 0 | 0 | 0 | 0 | 5/5 | 5/5 | 10/10 |
| 600 | 0 | 0 | 3 | 5 | 2 | 0 | 0 | 0 | 0 | 0 | 0 | 0 | 0 | 0 | 0 | 0 | 5/5 | 5/5 | 10/10 |

[a]Parent Compound Control
[b]Death occurred on Day 12
M—Male
F—Female

The intravenous $LD_{10}$ of IPM Lysine Salt was calculated to be 133 mg/kg (95% confidence limits of 65 to 172) in mice (combined sexes), while the intravenous $LD_{50}$ was calculated to be 220 mg/kg (95% confidence limits of 184 to 265 mg/kg).

The $LD_{10}$ values for males and females separately were 140 and 179 mg/kg, respectively (95% confidence limits of 12 to 199 mg/kg for males; could not be calculated for females), while the $LD_{50}$ values for males and females were 247 and 197 mg/kg, respectively (95% confidence limits of 187 to 330 for males; could not be calculated for females).

No treatment-related macroscopic findings were noted in either sex in postmortem observations.

CONCLUSIONS

Mortality results generally displayed a typical dose-response effect, with IPM Lysine Salt being slightly more toxic in females than in males. No animals died at 50 or 75 mg/kg, 1 of 10 animals died at 100 mg/kg, 3 of 10 animals died at 200 mg/kg, 9 of 10 animals died at 300 mg/kg, and all animals died at 400, 500, and 600 mg/kg. The IPM parent compound control group exhibited the expected mortality (5 of 10 animals died), as well as greater toxicity in females than males, correlating with available data from previous studies. The onset of death in the study was slightly delayed, with the first mortalities occurring on Day 6 and the last on Day 12. Clinical signs generally reflecting the deteriorating state of mice prior to death were observed in both sexes. These clinical signs included moribundity, decreased activity, increased activity, swelling (tail, nose/muzzle, and/or face), breathing rapid/slow/shallow/difficult/audible, tremors, skin cold to touch, unkempt appearance, posture hunched, limb function impaired, hair discoloration in the dorsal and/or anogenital regions, feces few/absent, and urination decreased. Treatment-related decreases in mean body weight gain, or in many cases body weight loss, were noted in surviving animals by Day 7, with at least partial recovery by Day 14 in those animals surviving to study termination. No treatment-related macroscopic findings were noted at necropsy.

Based on the condition and findings of this study, the intravenous $LD_{10}$ of IPM 2Lys was calculated to be 133 mg/kg (95% confidence limits of 65 to 172) in mice (combined sexes), while the intravenous $LD_{50}$ was calculated to be 220 mg/kg (95% confidence limits of 184 to 265 mg/kg).

Example 7

This example summarizes the results of extensive preclinical data for the toxicity of IPM and its lysine salt. This data is used to design dosage regimens for human clinical trials.

The toxicity of IPM and its lysine salt have been investigated through pre-clinical acute and sub-acute studies using mice, rats and dogs. Single dose oral, intravenous (IV) and intraperitoneal (IP) routes of administration for IPM have been studied in mice and rats. Multiple daily dose administrations—IV and IP—have been studied in mice and dogs. Sub-acute intravenous (3-day) dosing in the mouse and dog has provided the toxicology/pharmacokinetic information regarding toxicities and drug disturbances that were utilized in designing the administration and dose schedules in humans. Sub-acute IV (3-day) dosing with the IPM lysine salt was conducted in the mouse.

Based upon the results of the dose range finding study, higher doses of IPM were required to produce mortality than anticipated. For rats, the oral $LD_{50}$ values were calculated to be 4443 mg/kg for males, 2786 mg/kg for females and 3560 mg/kg for both sexes combined. In each case, the 95% confidence limits could be calculated.

For mice, oral $LD_{50}$ values were calculated to be 1014 mg/kg for males (95% confidence limits), 1962 mg/kg for females (95% confidence limits of 1523-2983 mg/kg) and 1432 mg/kg for both sexes combined (95% confidence limits of 1128-1742 mg/kg).

For rats, single dose intravenous $LD_{50}$ values were calculated to be 567 mg/kg for males, 400 mg/kg for females and 428 mg/kg for both sexes combined. In each case, the 95% confidence limits could not be calculated. For mice, intravenous $LD_{50}$ values were calculated to be 929 mg/kg for males (95% confidence limits), 484 mg/kg for females (95% confidence limits of 72-1364 mg/kg) and 688 mg/kg for both sexes combined (95% confidence limits of 398-1366 mg/kg).

Administration of IPM by IV and IP routes did result in acute deaths for mice, rats and dogs. Oral administration to mice and rats was also evaluated and $LD_{50}$ values were determined in the 1.4-3.5 g/kg range for these rodent species. Acute intravenous toxicity symptoms in mice, rats and dogs, included less appetite, diarrhea, decreased activity and death.

The acceptable doses from the three (3) day dosing studies were significantly different from the single dose schedule. The effects of the drug on bone marrow, spleen and renal tubular functions were evaluated. The impact of IPM on these organs appears to contribute to the cause of death in these two species. A summary is presented below.

A sub-acute IV study of IPM in mice provided information as to $LD_{10}$ values and toxicity that could occur in humans. The mortality results displayed a typical dose-response effect, with IPM being slightly more toxic in females than in males.

The intravenous $LD_{10}$ of IPM was calculated to be 119 mg/kg (with 95% confidence limits of 87-134 mg/kg) in mice (combined sexes), while the intravenous $LD_{50}$ was calculated to be 149 mg/kg (with 95% confidence limits of 132-169 mg/kg). The $LD_{10}$ values for males and females separately were 168 and 125 mg/kg, respectively, while the $LD_{50}$ values for males and females were 176 and 132, respectively. In each case, the 95% confidence limits could not be calculated.

The sub-acute IPM lysine salt study included a total of 40 male and 40 female mice (Crl: CD-1(1CR)BR) weighing 24.8 to 29.1 g and 21.5 and 24.2 g, respectively, at randomization) were treated with doses of 50 to 600 mg/kg IV daily×3 days.

For IPM LYS salt, the intravenous $LD_{10}$ for the 3-day mouse study was calculated to be 133 mg/kg (95% confidence limits 65 to 172 mg/kg (combined sexes)), while the intravenous $LD_{50}$ was 220 mg/kg (with 95% confidence limits of 184 to 265 mg/kg (for combined sexes)). The $LD_{10}$ values for males and females separately were 140 and 179 mg/kg, respectively (95% confidence limits of 12 to 199 mg/kg for males; could not be calculated for females). The $LD_{50}$ values for males and females were 247 and 197 mg/kg, respectively (95% confidence limits of 187 to 330 for males; could not be calculated for females).

The IPM lysine salt generally displayed a typical dose-response effect, with slightly more toxicity seen in females. No mice died at 50, 75 or 200 mg/kg, 1 of 10 animals died at 100 mg/kg, 9 out of 10 animals died at 300 mg/kg, and all mice died at 400, 500, and 600, mg/kg. The parent IPM control group exhibited the expected mortality, as well as greater toxicity in females than males, correlating with available data from previous studies. The onset of death in the study was slightly delayed, with the first mortalities occurring on Day 6 and the last on Day 12. Clinical signs, generally reflecting the deteriorating state of mice prior to death, were observed in both sexes. Based on the findings of microscopic examination, IPM administered alone or as the lysine salt IV daily for three days produced treatment-related bone marrow depletion, kidney tubular necrosis, or a combination of both and were considered the cause of death. For IPM, severe bone marrow depletion was present in males at 178 mg/kg and higher, and in females at 133 mg/kg and higher. Kidney tubular necrosis occurred in males at 237 mg/kg and higher, and in females at 133 mg/kg and higher. In addition, splenic lymphoid depletion was noted in most males and in all females that died during the study. No obvious treatment-related microscopic findings were noted in either sex at 75 mg/kg. Clinical signs generally secondary to the deteriorating state of the mice prior to death were observed but no clear evidence of body weight effects were seen in mice surviving to study termination.

The intravenous $LD_{10}$ for isophosphoramide mustard (IPM) and its lysine salt administered daily for three days were calculated to be 119 mg/kg vs. 133 mg/kg, respectively, with $LD_{50}$ calculated as 149 mg/kg vs. 220 mg/kg, respectively.

Acute and sub-acute toxicity studies in rodents and dogs have been performed with IPM and its lysine salt. These studies also have been used to develop acceptable starting doses human investigations. A summary of the rodent and dog toxicity data for IV administration of IPM is recorded in Table 15a and a summary of the mouse toxicity data for IV administration of IPM.(LYS)$_2$ is recorded in Table 16a.

TABLE 15a

Summary of Intravenous Treatment Experience—IPM

| # and Specie | Dose, Regimen and Duration | Total Dose of IPM (mg) | Plasma IPM | Efficacy | Safety $LD_{50}$ (mg/kg) |
|---|---|---|---|---|---|
| 47 Rats | 400-2,000 mg/kg; Iv × 1d | 81.6-650 | Not Tested | Not Tested | 428 |

TABLE 15a-continued

Summary of Intravenous Treatment Experience—IPM

| # and Specie | Dose, Regimen and Duration | Total Dose of IPM (mg) | Plasma IPM | Efficacy | Safety $LD_{50}$ (mg/kg) |
|---|---|---|---|---|---|
| 40 Mice | 100-1,200 mg/kg; Iv × 1d | 3.2-36 | Not Tested | Not Tested | 688 |
| 80 Mice | 75-562 mg/kg; iv daily × 3 days | 5.7-60.6 | Not Tested | Not Tested | 149 |
| 14 Dogs | 1-100 mg/kg/d; iv daily × 3 days | 22.5-2130 | 100 mg/kg/day × 3 days ($C_{max}$ 25-78 mcg/ml) | Not Tested | 1-5 mg/kg/day × 3 days (100% survival) |

TABLE 16a

Intravenous IPM Lysine Salt

| # and Specie | Dose, Regimen and Duration | Total Dose of IPM (mg) | Plasma IPM | Efficacy | Safety $LD_{50}$ (mg/kg) |
|---|---|---|---|---|---|
| 80 Mice | 50-600 mg/kg/d; iv daily × 3 days | 4.3-80 | Not Tested | Not Tested | 220 |

The IPM MTD for dogs was 5 mg/kg/day×3 days and a correspondence starting dose in humans of 100 mg/m$^2$ per day for three (3) days should be a safe starting point. For IPM.(LYS)$_2$, the $LD_{10}$ for the intravenous three (3) day dose schedule in the mouse was calculated to be ~133 mg/kg/day×3 days. IPM.(LYS)$_2$ is considered to be a minimally toxic alkylating agent with a steep therapeutic range. On mg/kg basis, the mean toxic dose (MTD) in humans for the lysine salt is estimated as 1/10 the $LD_{10}$ in mice or 40 mg/m$^2$/d.

Estimated comparable human IV dosages are recorded in Table 17a.

TABLE 17a

Estimated Comparable Human Intravenous Dosages

| Drug | Species | Sub-acute IV $LD_{10}$ | Comparable Human IV Dosage |
|---|---|---|---|
| IPM | Mouse | 119 mg/kg/d | 30 mg/m$^2$/d |
| IPM | Dog | 5 mg/kg/d | 100 mg/m$^2$/d |
| IPM Lysine Salt | Mouse | 133 mg/kg/d | 40 mg/m$^2$/d |

Example 8

This example describes the treatment of cancer in human subjects having metastatic ovarian cancer.

The subject is treated with IPM 500 mg/m$^2$ daily for three consecutive days via intravenous infusion. Her serum electrolytes, such as phosphorus and chloride, are corrected with supplemental electrolytes, which are discontinued after seven days. BUN and creatinine are monitored normal limits.

Example 9

This example describes the results of treating human subjects with IPM.(LYS)$_2$.

To date four (4) patients with advanced cancer have been treated with IPM.(LYS)$_2$.

The initial dose of IPM lysine salt was 30 mg/m$^2$ and was administrated intravenously daily for three (3) days. One patient (cohort) was treated per dose escalation every 21-28 days to allow for toxicity presentation. Doses were escalated by 40% if there were no serious toxic events. Four patients have been treated—one at each dosage—30, 42, 59 and 83 mg/m$^2$ via daily IV administration for 3 days without serious toxicity. One patient with rectal cancer had stabilization of his disease following administration of 83 mg/m$^2$ of IPM.(LYS)$_2$ via daily IV administration for 3 days.

Example 10

This example describes the treatment of non-small cell lung cancer which has progressed to metastatic infiltrating moderately differentiated adenocarcinoma. The status of the disease can be confirmed by CAT scan.

Isophosphoramide mustard lysine salt is administered at 350 mg/m$^2$ daily for three consecutive days intravenously. After a 21-day rest period, the three-day treatment protocol is repeated once. Daily blood fluid chemistry and hematological studies are monitored during treatments. The status of the cancer is monitored by CAT scan.

Exemplary Formulations

I. Formulation Development

IPM tris drug formulation comprises a blend of IPM tris salt, Microcrystalline Cellulose (Avicel PH112), Sodium Croscarmellose (Ac-Di-Sol) and Magnesium Stearate (vegetable source).

A. Batch Formulation of 10 mg Strength Tris IPM Capsules

TABLE 1

Quantitative Composition of IPM Tris Capsule Drug Product—10 mg strength

| Component | Reference to Quality Standard | Function | Amount per Batch (10 mg strength) | Amount per Capsule (10 mg strength) |
|---|---|---|---|---|
| IPM-tris salt | In-house standard | API | 154.0 g[1] | 15.4 mg |
| Microcrystalline Cellulose, NF (Avicel PH112) | NF | Diluent | 1912.0 g | 191.2 mg |
| Croscarmellose Sodium, NF (Ac-Di-Sol) | NF | Water-absorbing agent; capsule disintegrant | 21.0 g | 2.1 mg |
| Magnesium Stearate, NF, Ph. Eur. (Vegetable Source— Grade 905-G) | NF | Lubricant | 10.5 g | 1.05 mg |
| Total | | | 2097.5 g/ batch | 209.75 mg/ capsule |
| Size 1, hard-gelatin white opaque capsule | Capsugel certificate of conformance | Product delivery | 10,000 capsules | 1 capsule |

[1]154 g of IPM tris salt (molecular weight = 342.16) will deliver 100.0 g of IPM active pharmaceutical ingredient (molecular weight = 221.0).
API = active pharmaceutical ingredient;
NA = not available;
NF = National Formulary.

B. Batch Analysis of 10 mg Tris IPM Capsules
Product: Tris IPM capsules of Table 1
Lot Disposition: Stability, CTM
Stability Storage Condition: −20° C., 5° C. or 25° C./60% RH

TABLE 2

Batch Analyses of IPM Tris Drug Product

| Test | cGMP Batch |
|---|---|
| Appearance | Size 1 hard shell white opaque capsule, containing white to off-white powder |
| Brittleness | No cracking or breaking observed |
| Identification (HPLC Retention Time) | 0.999 |
| Potency by HPLC (Assay) | 98.3% (mean IPM active per capsule: 9.8 mg) |
| Purity | 100.0% |
| Related Substances (LC/MS) | No impurities, 0.0% |
| Capsule Weight (mg) | Capsule 1: 285.46 |
| | Capsule 2: 283.69 |
| | Capsule 3: 289.99 |
| | Capsule 4: 286.17 |
| | Capsule 5: 287.22 |
| | Capsule 6: 289.43 |
| | Capsule 7: 285.23 |
| | Capsule 8: 286.80 |
| | Capsule 9: 277.25 |
| | Capsule 10: 288.25 |
| | Mean: 285.95 |
| Content Uniformity | Capsule 1: 99.0% |
| | Capsule 2: 96.6% |
| | Capsule 3: 93.1% |
| | Capsule 4: 93.2% |
| | Capsule 5: 104.1% |
| | Capsule 6: 102.9% |
| | Capsule 7: 96.7% |
| | Capsule 8: 101.4% |
| | Capsule 9: 98.0% |
| | Capsule 10: 97.9% |
| | Mean: 98.3% |
| Disintegration | Vessel #/Rupture Time |
| | 1 . . . 1 min 43 sec |
| | 2 . . . 1 min 37 sec |
| | 3 . . . 1 min 41 sec |
| | 4 . . . 1 min 35 sec |
| | 5 . . . 1 min 39 sec |
| | 6 . . . 1 min 48 sec |
| Water Content | 1.2% |
| Microbial Limits: | |
| Total Aerobic Count | Less than 10 CFU/g of specimen |
| Total combined yeast and molds | 20 CFU/g of specimen |
| P. aeruginosa | Absent |
| E. coli | Absent |
| S. aureus | Absent |
| Salmonella sp. | Absent |

NA = not available;
HPLC = high-performance liquid chromatography;
CFU = colony forming unit;
RRT = relative retention time

TABLE 3

Summary of −20° C. Stability Data for 10 mg IPM Tris capsules

| | Results | | | |
|---|---|---|---|---|
| Test | Initial | 0.5 mo | 1.0 mo | 3.0 mo |
| Identification (HPLC) | 1.00 | 1.00 | 1.00 | 1.00 |
| Potency by HPLC (Assay) | 98.3% (mean IPM active per capsule: 9.8 mg) | 105.3% (mean IPM active per capsule: 10.5 mg) | 102.1% (mean IPM active per capsule: 10.2 mg) | 103.1% (mean IPM active per capsule: 10.3 mg) |

TABLE 3-continued

Summary of −20° C. Stability Data for 10 mg IPM Tris capsules

| | Results | | | |
|---|---|---|---|---|
| Test | Initial | 0.5 mo | 1.0 mo | 3.0 mo |
| Purity (% area) | 100.0% | NA | NA | 99.9% |
| Related Substances (% area) | ND | NA | NA | RRT 0.56 = 0.09% |
| Total Related Substances | 0.0% | NA | NA | 0.1% |
| Water Content | 1.2% | 1.1% | 2.0% | 3.5% |

CTM = clinical trials material;
HPLC = high-performance liquid chromatography;
ND = not detected;
RRT = relative retention time;
NA = not available

TABLE 4

Summary of 5° C. Stability Data for 10 mg IPM Tris capsules

| | Results | | | |
|---|---|---|---|---|
| Test | Initial | 0.5 mo | 1.0 mo | 3.0 mo |
| Identification (HPLC) | 1.00 | 1.00 | 1.01 | 1.00 |
| Potency by HPLC (Assay) | 98.3% (mean IPM active per capsule: 9.8 mg) | 98.2% (mean IPM active per capsule: 9.8 mg) | 94.8% (mean IPM active per capsule: 9.5 mg) | 101.8% (mean IPM active per capsule: 10.2 mg) |
| Purity (% area) | NA | 99.9% | NA | 99.9% |
| Related Substances (% area) | NA | RRT 0.558: 0.06% | NA | RRT 0.56 = 0.08% |
| Total Related Substances | NA | 0.1% | NA | 0.1% |
| Water Content | 1.2% | 1.3% | 1.8% | 4.2% |

HPLC = high-performance liquid chromatography;
ND = not detected;
RRT = relative retention time;
NA = not available

TABLE 5

Summary of 25° C. Stability Data for 10 mg IPM Tris Capsules

| | Results | | | |
|---|---|---|---|---|
| Test | Initial | 0.5 mo | 1.0 mo | 3.0 mo |
| Identification (HPLC) | 1.00 | 1.00 | 1.00 | 1.00 |
| Potency by HPLC (Assay) | 98.3% (mean IPM active per capsule: 9.8 mg) | 95.4% (mean IPM active per capsule: 9.5 mg) | 100.9% (mean IPM active per capsule: 10.1 mg) | 79.4% (mean IPM active per capsule: 7.9 mg) |
| Purity (% area) | NA | NA | NA | 99.0% |
| Related Substances (% area) | NA | NA | NA | RRT 4.26 = 0.22% RRT 0.57 = 0.12% RRT 4.56 = 0.14% RRT 5.10 = 0.2% |
| Total Related Substances | NA | NA | NA | 1.0% |
| Water Content | 1.2% | 2.0% | 2.6% | 3.8% |

CTM = clinical trials material;
HPLC = high-performance liquid chromatography;
ND = not detected;
RRT = relative retention time;
NA = not available

C. Batch Analysis of 50 mg Tris IPM Capsules

TABLE 6

Batch analysis of 50 mg Tris IPM capsules

| Test | cGMP Batch |
|---|---|
| Appearance | Size 1 hard shell opaque capsule, containing white to off-white powder |
| Brittleness | No cracking or breaking observed |
| Identification (HPLC Retention Time) | 1.002 |
| Potency by HPLC (Assay) | 102.8%, 51.4 mg/capsule. |
| Purity | 100.0% |
| Related Substances (LC/MS) | Total impurities—None Detected |
| Capsule Weight (mg) | Capsule 1: 286.87<br>Capsule 2: 276.81<br>Capsule 3: 271.31<br>Capsule 4: 283.70<br>Capsule 5: 291.33<br>Capsule 6: 277.61<br>Capsule 7: 281.76<br>Capsule 8: 279.91<br>Capsule 9: 285.73<br>Capsule 10: 272.00<br>Mean: 280.70 |
| Content Uniformity | Capsule 1: 102.0%<br>Capsule 2: 97.6%<br>Capsule 3: 97.8%<br>Capsule 4: 107.8%<br>Capsule 5: 111.4%<br>Capsule 6: 101.9%<br>Capsule 7: 101.1%<br>Capsule 8: 104.2%<br>Capsule 9: 105.9%<br>Capsule 10: 97.9%<br>Mean: 102.8% |
| Water Content | 2.4% |
| Microbial Limits: | |
| Total Aerobic Count | <10 cfu/g |
| Total combined yeast and molds | 20 cfu/g |
| P. aeruginosa | Absent |
| E. coli | Absent |
| S. aureus | Absent |
| Salmonella sp. | Absent |

TABLE 7

Summary of −20° C. Stability Data for 50 mg IPM Tris Capsules

| | Results | | |
|---|---|---|---|
| Test | Initial | 0.5 mo | 1.0 mo |
| Identification (HPLC) | RRT = 0.98 to 1.02 | NA | 1.00 |
| Potency by HPLC (Assay) | 98.3% (mean IPM active per capsule: 9.8 mg) | NA | 101% (mean IPM active per capsule: 50.6 mg) |

TABLE 7-continued

Summary of −20° C. Stability Data for 50 mg IPM Tris Capsules

| Test | Results | | |
|---|---|---|---|
| | Initial | 0.5 mo | 1.0 mo |
| Purity (% area) | NA | NA | 100.0% |
| Related Substances (% area) Individual | NA | NA | ND |
| Total Related Substances | NA | NA | ND |
| Water Content | 2.4% | 2.5% | 2.0% |

NA = not available;
HPLC = high-performance liquid chromatography

TABLE 8

Summary of 5° C. Stability Data for 50 mg IPM Tris Capsules

| Test | Results | | |
|---|---|---|---|
| | Initial | 0.5 mo | 1.0 mo |
| Identification (HPLC) | RRT = 0.98 to 1.02 | NA | 1.00 |
| Potency by HPLC (Assay) | 98.3% (mean IPM active per capsule: 9.8 mg) | NA | 96% (mean IPM active per capsule: 48.1 mg) |
| Purity (% area) | NA | NA | 99.9% |
| Related Substances (% area) | NA | NA | 0.1% |

TABLE 8-continued

Summary of 5° C. Stability Data for 50 mg IPM Tris Capsules

| Test | Results | | |
|---|---|---|---|
| | Initial | 0.5 mo | 1.0 mo |
| Total Related Substances | NA | NA | 0.1% |
| Water Content | 2.4% | 2.4% | 2.4% |

NA = not available;
HPLC = high-performance liquid chromatography

TABLE 9

Summary of 25° C./60% RH Stability Data for 50 mg IPM Tris Capsules

| Test | Results | | |
|---|---|---|---|
| | Initial | 0.5 mo | 1.0 mo |
| Identification (HPLC) | RRT = 0.98 to 1.02 | NA | 1.00 |
| Potency by HPLC (Assay) | 98.3% (mean IPM active per capsule: 9.8 mg) | NA | 97% (mean IPM active per capsule: 48.4 mg) |
| Purity (% area) | NA | NA | 99.9% |
| Related Substances (% area) Individual | NA | NA | 0.1% |
| Total Related Substances | NA | NA | 0.1% |
| Water Content | 2.4% | 2.5% | 2.8% |

NA = not available;
HPLC = high-performance liquid chromatography

D. Batch Analysis of 10 mg Tris IPM Capsules

TABLE 10

Summary of −20° C. Stability Data for 10 mg Palifosfamide Tris (Tris(hydroxymethyl)aminomethane (Tris)) Capsules ≤3 month

| Test | Results | | | | |
|---|---|---|---|---|---|
| | Initial | 0.5 mo | 1 mo | 2 mo | 3 mo |
| Appearance | Conforms | Conforms | Conforms | Conforms | Conforms |
| Brittleness | Conforms | Conforms | Conforms | Conforms | Conforms |
| Identification (HPLC) | 1.00 | 1.00 | 1.00 | Not tested | 1.01 |
| Potency by HPLC (Assay) | 98.3% (mean IPM/cap: 9.8 mg) | 105.3% (mean IPM/cap: 10.5 mg) | 102.1% (mean IPM/cap: 10.2 mg) | Not tested | 103.1% (mean IPM/cap: 10.3 mg) |
| Purity (% area) | 100.0% | 99.9% | 99.9% | Not tested | 99.9% |
| Related Substances (% area) Individual | Not detected | RRT 0.555: 0.06% | RRT 2.198: 0.05% | Not tested | RRT 0.560: 0.09% |
| Total Related Substances | 0.0% | 0.1% | 0.1% | Not tested | 0.1% |

| | Vessel | Rupture Time | Vessel | Rupture Time | Vessel | Rupture Time | | |
|---|---|---|---|---|---|---|---|---|
| Dissolution (Capsule Rupture Method) | 1 | 1 min 43 sec | 1 | 53 sec | 1 | 1 min 38 sec | Not tested | Not tested |
| | 2 | 1 min 41 sec | 2 | 1 min 19 sec | 2 | 1 min 26 sec | | |
| | 3 | 1 min 35 sec | 3 | 1 min 25 sec | 3 | 1 min 38 sec | | |
| | 4 | 1 min 35 sec | 4 | 1 min 10 sec | 4 | 1 min 0 sec | | |
| | 5 | 1 min 39 sec | 5 | 1 sec | 5 | 1 min 26 sec | | |
| | | | 6 | 40 sec | | | | |

TABLE 10-continued

Summary of −20° C. Stability Data for 10 mg Palifosfamide Tris (Tris(hydroxymethyl)aminomethane (Tris)) Capsules ≤3 month

| Test | Initial | | 0.5 mo | 1 mo | | 2 mo | 3 mo |
|---|---|---|---|---|---|---|---|
| | 6 | 1 min 48 sec | | 6 | 1 min 17 sec | | |
| Dissolution (HPLC) | 20 min Mean % LC: 67.1% Mean IPM/cap: 6.7 mg 40 min Mean % LC: 59.3% Mean IPM/cap: 5.9 mg 60 min Mean % LC: 53.4% Mean IPM/cap: 5.3 mg | | Not tested | Not tested | | Not tested | 20 min Mean % LC: 78.1% Mean IPM/cap: 7.8 mg 40 min Mean % LC: 66.4% Mean IPM/cap: 6.6 mg 60 min Mean % LC: 58.8% Mean IPM/cap: 5.9 mg |
| Water Content | 1.2% | | 1.1% | 2.0% | | 2.5% | 3.5% |

HPLC = high-performance liquid chromatography;
RRT = relative retention time

TABLE 11

Summary of −20° C. Stability Data for 10 mg Palifosfamide Tris (Tris(hydroxymethyl)aminomethane (Tris)) Capsules, 6-12 month

| Test | Initial | | 6 mo | 9 mo | 12 mo |
|---|---|---|---|---|---|
| Appearance | Conforms | | Conforms | Conforms | Conforms |
| Brittleness | Conforms | | Conforms | Conforms | Conforms |
| Identification (HPLC) | 1.00 | | 1.00 | 1.00 | 1.00 |
| Potency by HPLC (Assay) | 98.3% (mean IPM/cap: 9.8 mg) | | 96.3.3% (mean IPM/cap: 9.6 mg) | 94.8% (mean IPM/cap: 9.5 mg) | 101.9% (mean IPM/cap: 10.2 mg) |
| Purity (% area) | 100.0% | | 99.8% | 99.8% | 99.8% |
| Related Substances (% area) Individual | Not detected | | RRT 0.578: 0.17% | RRT 2.798: 0.08% RRT 0.610: 0.05% RRT 6.189: 0.05% | RRT 2.546: 0.05% RRT 0.382: 0.07% RRT 6.083: 0.05% |
| Total Related Substances | 0.0% | | 0.2% | 0.2% | 0.2% |
| | Vessel | Rupture Time | | | |
| Dissolution (Capsule Rupture Method) | 7 8 9 10 11 12 | 1 min 43 sec 1 min 37 sec 1 min 41 sec 1 min 35 sec 1 min 39 sec 1 min 48 sec | Not tested | Not tested | Not tested |
| Dissolution (HPLC) | 20 min Mean % LC: 67.1% Mean IPM/cap: 6.7 mg 40 min Mean % LC: 59.3% | | 20 min Mean % LC: 79.4% Mean IPM/cap: 7.9 mg 40 min Mean % LC: 66.3% | 20 min Mean % LC: 67.5% Mean IPM/cap: 6.8 mg 40 min Mean % LC: 56.0% | 20 min Mean % LC: 69.6% Mean IPM/cap: 7.0 mg 40 min Mean % LC: 58.6% |

TABLE 11-continued

Summary of −20° C. Stability Data for 10 mg Palifosfamide Tris (Tris(hydroxymethyl)aminomethane (Tris)) Capsules, 6-12 month

| Test | Initial | 6 mo | 9 mo | 12 mo |
|---|---|---|---|---|
| | Mean IPM/cap: 5.9 mg 60 min Mean % LC: 53.4% Mean IPM/cap: 5.3 mg | Mean IPM/cap: 6.6 mg 60 min Mean % LC: 57.0% Mean IPM/cap: 5.7 mg | Mean IPM/cap: 5.6 mg 60 min Mean % LC: 48.0% Mean IPM/cap: 4.8 mg | Mean IPM/cap: 5.9 mg 60 min Mean % LC: 51.6% Mean IPM/cap: 5.2 mg |
| Water Content | 1.2% | 2.9% | 3.7% | 3.5% |

HPLC = high-performance liquid chromatography;
RRT = relative retention time

TABLE 12

Summary of 5° C. Stability Data for 10 mg Palifosfamide Tris (Tris(hydroxymethyl)aminomethane (Tris)) Capsules, ≤3 month

| Test | Initial | 0.5 mo | 1 mo | 2 mo | 3 mo |
|---|---|---|---|---|---|
| Appearance | Conforms | Conforms | Conforms | Conforms | Conforms |
| Brittleness | Conforms | Conforms | Conforms | Conforms | Conforms |
| Identification (HPLC) | 1.00 | 1.00 | 1.00 | 1.00 | 1.00 |
| Potency by HPLC (Assay) | 98.3% (mean IPM/cap: 9.8 mg) | 98.2% (mean IPM/cap: 9.8 mg) | 94.8% (mean IPM/cap: 9.5 mg) | Not tested | 101.8% (mean IPM/cap: 10.2 mg) |
| Purity (% area) | 100% | 99.9% | 99.9% | Not tested | 99.9% |
| Related Substances (% area) Individual | Not detected | RRT 0.558: 0.06% | NA | Not tested | RRT 0.561: 0.08% |
| Total Related Substances | 0.0% | 0.1% | 0.1% | Not tested | 0.1% |

| | Vessel | Rupture Time | Vessel | Rupture Time | Vessel | Rupture Time | | |
|---|---|---|---|---|---|---|---|---|
| Dissolution (Capsule Rupture Method) | 1 | 1 min 43 sec | 1 | 1 min 10 sec | 1 | 1 min 11 sec | Not tested | Not tested |
| | 2 | 1 min 37 sec | 2 | 51 sec | 2 | 1 min 24 sec | | |
| | 3 | 1 min 41 sec | 3 | 1 min 5 sec | 3 | 1 min 18 sec | | |
| | 4 | 1 min 35 sec | 4 | 1 min 9 sec | 4 | 1 min 1 sec | | |
| | 5 | 1 min 39 sec | 5 | 1 min 29 sec | 5 | 1 min 24 sec | | |
| | 6 | 1 min 48 sec | 6 | 1 min 19 sec | 6 | 47 sec | | |

| Test | Initial | 0.5 mo | 1 mo | 2 mo | 3 mo |
|---|---|---|---|---|---|
| Dissolution (HPLC) | 20 min Mean % LC: 67.1% Mean IPM/cap: 6.7 mg 40 min Mean % LC: 59.3% Mean IPM/cap: 5.9 mg 60 min Mean % LC: 53.4% Mean IPM/cap: 5.3 mg | Not tested | Not tested | 20 min Mean % LC: 65.5% Mean IPM/cap: 6.6 mg 40 min Mean % LC: 59.0% Mean IPM/cap: 5.9 mg 60 min Mean % LC: 53.6% Mean IPM/cap: 5.4 mg | 20 min Mean % LC: 72.9% Mean IPM/cap: 7.3 mg 40 min Mean % LC: 65.0% Mean IPM/cap: 6.5 mg 60 min Mean % LC: 58.1% Mean IPM/cap: 5.8 mg |
| Water Content | 1.2% | 1.3% | 1.8% | 2.3% | 4.2% |

HPLC = high-performance liquid chromatography;
NA = not applicable (None ≥ 0.1%);
RRT = relative retention time

TABLE 13

Summary of 5° C. Stability Data for 10 mg Palifosfamide Tris
(Tris(hydroxymethyl)aminomethane (Tris)) Capsules, 6-12 month

| Test | Initial | 6 mo | 9 mo | 12 mo |
|---|---|---|---|---|
| | | Results | | |
| Appearance | Conforms | Conforms | Conforms | Conforms |
| Brittleness | Conforms | Conforms | Conforms | 1 of 6 capsules cracked |
| Identification (HPLC) | 1.00 | 1.00 | 1.00 | 1.00 |
| Potency by HPLC (Assay) | 98.3% (mean IPM/cap: 9.8 mg) | 94.4% (mean IPM/cap: 9.4 mg) | 92.4% (mean IPM/cap: 9.3 mg) | 97.9% (mean IPM/cap: 9.8 mg) |
| Purity (% area) | 100% | 99.8% | 99.8% | 99.9% |
| Related Substances (% area) Individual | Not detected | RRT 0.576: 0.13% | RRT 2.822: 0.06% RRT 0.579: 0.06% RRT 8.294: 0.03% | RRT 2.651: 0.05% RRT 0.391: 0.07% |
| Total Related Substances | 0.0% | 0.2% | 0.2% | 0.1% |
| Dissolution (HPLC) | 20 min Mean % LC: 67.1% Mean IPM/cap: 6.7 mg 40 min Mean % LC: 59.3% Mean IPM/cap: 5.9 mg 60 min Mean % LC: 53.4% Mean IPM/cap: 5.3 mg | 20 min Mean % LC: 69.7% Mean IPM/cap: 7.0 mg 40 min Mean % LC: 60.6% Mean IPM/cap: 6.1 mg 60 min Mean % LC: 53.6% Mean IPM/cap: 5.4 mg | 20 min Mean % LC: 70.8% Mean IPM/cap: 7.1 mg 40 min Mean % LC:57.6% Mean IPM/cap: 5.8 mg 60 min Mean % LC:48.1% Mean IPM/cap: 4.8 mg | 20 min Mean % LC: 68.4% Mean IPM/cap: 6.8 mg 40 min Mean % LC: 58.9% Mean IPM/cap: 5.9 mg 60 min Mean % LC: 50.8% Mean IPM/cap: 5.1 mg |
| Water Content | 1.2% | 2.6% | 3.9% | 3.5% |

HPLC = high-performance liquid chromatography;
RRT = relative retention time

TABLE 14

Summary of 25° C. Stability Data for 10 mg Palifosfamide Tris
(Tris(hydroxymethyl)aminomethane (Tris)) Capsules ≤3 month

| Test | Initial | 0.5 mo | 1 mo | 2 mo | 3 mo |
|---|---|---|---|---|---|
| | | | Results | | |
| Appearance | Conforms | Conforms | Conforms | Conforms | Conforms |
| Brittleness | Conforms | Conforms | Conforms | Conforms | Conforms |
| Identification (HPLC) | 1.00 | 1.00 | 1.01 | 1.00 | 1.00 |
| Potency by HPLC (Assay) | 98.3% (mean IPM/cap: 9.8 mg) | 95.4% (mean IPM/cap: 9.5 mg) | 100.9% (mean IPM/cap: 10.1 mg) | Not tested | 79.4% (mean IPM/cap: 7.9 mg) |
| Purity (% area) | 100.0% | 99.9% | 99.9% | Not tested | 99.0% |
| Related Substances (% area) Individual | NA | RRT 0.558: 0.06% | NA | Not tested | RRT 4.264: 0.22% RRT 0.568: 0.12% RRT 4.562: 0.14% RRT 5.104: 0.20% |
| Total Related Substances | 0.0% | 0.1% | 0.1% | Not tested | 1.0% |

| | Vessel | Rupture Time | Vessel | Rupture Time | Vessel | Rupture Time | | |
|---|---|---|---|---|---|---|---|---|
| Dissolution (Capsule Rupture Time) | 1 | 1 min 43 sec | 1 | 1 min 10 sec | 1 | 57 sec | Not tested | Not tested |
| | 2 | 1 min 37 sec | 2 | 1 min 3 sec | 2 | 1 min 7 sec | | |
| | 3 | 1 min 41 sec | 3 | 1 min 20 sec | 3 | 1 min 14 sec | | |
| | 4 | 1 min 35 sec | 4 | 1 min 25 sec | 4 | 1 min 39 sec | | |
| | 5 | 1 min 39 sec | 5 | 1 min 9 sec | 5 | 1 min 20 sec | | |
| | | | | | 6 | 49 sec | | |

TABLE 14-continued

Summary of 25° C. Stability Data for 10 mg Palifosfamide Tris (Tris(hydroxymethyl)aminomethane (Tris)) Capsules ≤3 month

| Test | Initial | 0.5 mo | 1 mo | 2 mo | 3 mo |
|---|---|---|---|---|---|
| | 6  1 min 48 sec | 6  52 sec | | | |
| Dissolution (HPLC) | 20 min Mean % LC: 67.1% Mean IPM/cap: 6.7 mg 40 min Mean % LC: 59.3% Mean IPM/cap: 5.9 mg 60 min Mean % LC: 53.4% Mean IPM/cap: 5.3 mg | Not tested | Not tested | 20 min Mean % LC: 70.2% Mean IPM/cap: 7.0 mg 40 min Mean % LC: 61.3% Mean PM/cap: 6.1 mg 60 min Mean % LC: 56.7% Mean IPM/cap: 5.7 mg | 20 min Mean % LC: 59.5% Mean IPM/cap: 6.0 mg 40 min Mean % LC: 54.1% Mean IPM/cap: 5.4 mg 60 min Mean % LC: 49.1% Mean IPM/cap: 4.9 mg |
| Water Content | 1.2% | 2.0% | 2.6% | 2.3% | 3.8% |

HPLC = high-performance liquid chromatography;
NA = not applicable (None ≥ 0.1%);
RRT = relative retention time

TABLE 15

Summary of 25° C. Stability Data for 10 mg Palifosfamide Tris (Tris(hydroxymethyl)aminomethane (Tris))Capsules 6-12 month

| Test | Initial | 6 mo | 9 mo | 12 mo |
|---|---|---|---|---|
| Appearance | Conforms | Conforms | Conforms | Conforms |
| Brittleness | Conforms | Conforms | Conforms | Conforms |
| Identification (HPLC) | 1.00 | 0.98 | Not tested | Not tested |
| Potency by HPLC (Assay) | 98.3% (mean IPM/cap: 9.8 mg) | 32.8% (mean IP M/cap: 3.3 mg) | Not tested | Not tested |
| Purity (% area) | 100.0% | 1.6% | Not tested | Not tested |
| Related Substances (% area) Individual | NA | ** | Not tested | Not tested |
| Total Related Substances | 0.0% | 98.4% | Not tested | Not tested |
| Dissolution (HPLC) | 20 min Mean % LC: 67.1% Mean IPM/cap: 6.7 mg 40 min Mean % LC: 59.3% Mean IPM/cap: 5.9 mg 60 min Mean % LC: 53.4% Mean IPM/cap: 5.3 mg | 20 min Mean % LC: 0.0% Mean IPM/cap: ND* 40 min Mean % LC: 0.0% Mean IPM/cap: ND * 60 min Mean % LC: 0.0% Mean IPM/cap: ND * | Not tested | Not tested |
| Water Content | 1.2% | 2.6% | 3.9% | 3.5% |

HPLC = high-performance liquid chromatography;
RRT = relative retention time;
ND * = No IPM peak was detected

II. Synthetic Preparation of IPM Salts and Analogues Thereof

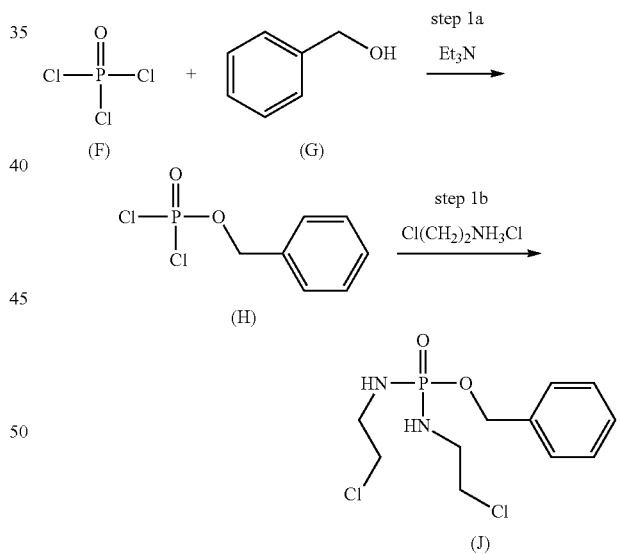

Procedure for the preparation of benzyl isophosphoramide (J): Into a 2 L 3-neck flask, 100 g of P(O)Cl$_3$ was charged, followed by addition of 400 mL of acetonitrile. The content was then cooled to −30±5° C. Into another flask, 70.5 g of benzyl alcohol and 90.7 mL of triethylamine (TEA) were added, followed by addition of 200 mL of acetonitrile and stir until the mixture becomes homogeneous. To the cold solution of P(O)Cl$_3$ was added the solution of benzyl alcohol and TEA via syringe pump while maintaining the reaction temperature at to −30±5° C. This addition lasts 140 min. After the addition, the reaction mixture was allowed to stir for 1 h at −30±5° C. To the reaction mixture, 151.3 g of ClCH$_2$CH$_2$NH$_3$Cl was weighed. Subsequently, 362.6 mL of TEA was charged over 140 min via syringe pump while maintaining the temperature at −30±5° C. After the addition, the reaction mixture was allowed to warm to room temperature and stirred for 1 h. The reaction mixture was filtered to remove triethylamine hydrochloride salt and the reactor rinsed with 3×200 mL acetonitrile. The filtrate was taken on to the next step without further purification.

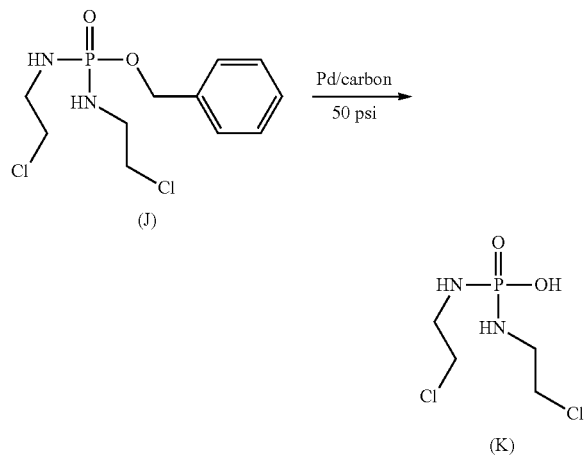

Procedure for the Preparation of Benzyl Isophosphoramide (K):

The filtrate resulting from step 1b above was transferred into a hydrogenation reactor and 3.4 g of Pd/C was charged. Hydrogenolysis was conducted under 50 psi of hydrogen. After 15 h, the reaction was complete and no Bz-IPM was observed (Note: The pH for the reaction mixture was 3-4). For work up and isolation of the product, the reaction mixture was transferred into a flask and the content was cooled to 0° C. to 10° C. To the cooled reaction mixture was added 100 mL (719.4 mmol, 1.1 equiv) of TEA to increase the pH to 9.5-10 (Note: This addition lasted less than 5 min). The resulting mixture was filtered to remove catalyst and rinsed with 2×100 mL of acetonitrile. The filtrate was cooled to 0° C. to 10° C., and to it 76 mL (924.5 mmol, 1.4 equiv) of 37% HCl was added to lower the pH to 1-2 (Note: This addition took 15 min). The resulting slurry was filtered and the wet cake was made into a slurry with two portions of 400 mL of 5% water in acetonitrile, and stirred for 5 min each. The wet cake was then rinsed with 3×200 mL of acetonitrile to give 105.8871 g (73.5%) product.

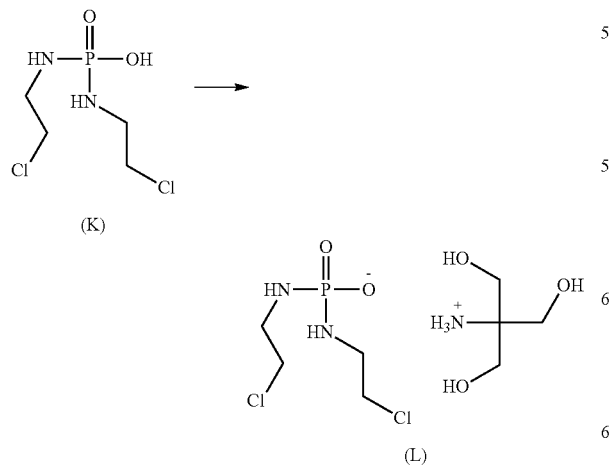

A. Procedure for the Preparation of IPM Salt (L):

Into a 250 mL 3-neck flask 26.5791 g of tris(hydroxymethyl)-aminomethane was added, followed by addition of 78.0 mL of N,N-DMF. The mixture was then heated to 100° C. to dissolve the base. After a clear solution formed, the batch was cooled to 20-25° C. (a slurry then formed). To the above slurry, 49.1322 g (98.7% purity based on NMR, 0.2194 moles) of IPM analogue (K) (1766-026-11) was weighed, and rinsed with 48 mL of N,N-DMF. The mixture was stirred for 1 h until a clear solution formed. The resulting solution proceeds polish filtration with Whatman #1 filter paper. The filtrate was transferred into a 2 L flask, and to it, 144 mL of acetonitrile was added over 5 min. To the batch 852 mL of methyl tert-butyl ether (MTBE) was introduced to form cloudy solution (Solid seeds were generated by scratching against the glass wall with a spatula). The batch was stirred for 1 h. The product was collected by filtration, followed by washing with 242 mL of MTBE in a yield of 72.3868 g (96.4%) as white solid. Residual palladium content was <10 ppm by ICP analysis.

B. Procedure for the Preparation of IPM Salt (L):

Into a 500 mL 3-neck flask, 54.1043 g of tris(hydroxymethyl)-aminomethane was added, followed by addition of 158 mL of N,N-DMF. The mixture was then heated to 100° C. to dissolve the base. After a clear solution formed, the batch was cooled to 20-25° C. (a slurry then formed). To the above slurry, 100.0135 g (98.7% purity based on NMR, 0.4466 moles) of IPM (1766-028-11) was weighed, and rinsed with 99 mL of N,N-DMF. The mixture was stirred for 140 min until a clear solution formed. The resulting solution proceeds polish filtration with Whatman #1 filter paper. The filtrate was transferred into a 5 L flask, and to it, 293 mL of acetonitrile was added over 5 min. To the batch, a slurry mixture of 0.3 g of salt L in 4.8 mL of DMF and 5.7 mL of acetonitrile was added. To the batch, 1734 mL of MTBE was introduced. The batch was stirred for 1 h. The product was collected by filtration, followed by washing with 494 mL of MTBE in a yield of 146.7 g (96.0%) as white solid.

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A method for the preparation of a compound of formula (D):

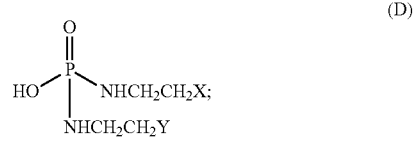

comprising treating a compound of formula (C):

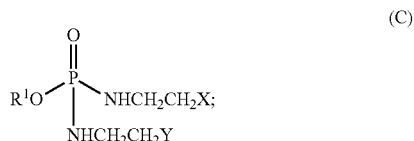

under hydrogenolysis conditions, wherein as valence and stability permit,

X and Y independently represent leaving groups;

R$^1$ is benzyl optionally substituted with one or more substituents selected from halogen, —R$^2$, —OR$^2$ and —NR$^2{}_2$ wherein R$^2$ is selected in each occurrence from H and lower alkyl; and the hydrogenolysis condition comprises a solvent system comprising one or more aprotic organic solvents.

2. The method of claim 1, wherein X and Y are both halogen.

3. The method of claim 2, wherein X and Y are both Cl.

4. The method of claim 1, wherein R$^1$ is unsubstituted benzyl.

5. The method of claim 1, wherein hydrogenolysis conditions comprise hydrogen gas and a hydrogenolysis catalyst.

6. The method of claim 5, wherein the hydrogenolysis catalyst comprises Pd.

7. The method of claim 5, wherein the hydrogenolysis catalyst comprises Pd/carbon.

8. The method of claim 1, wherein the hydrogenolysis conditions comprise hydrogen pressure greater than 1 atm.

9. The method of claim 8, wherein the pressure is less than or equal to 50 psi.

10. The method of claim 1, wherein the aprotic organic solvent is selected from the group consisting of acetone, 2-butanone, butyl acetate, ethyl acetate, acetonitrile, toluene, THF, dioxane, N,N-DMF, DMSO, 1,2-dichloroethane, and methylene chloride.

11. The method of claim 10, wherein the aprotic solvent is acetonitrile.

12. The method of claim 11, wherein acetonitrile represents more than about 10, 20, 30, 50, 70, 90, or 95% of the solvent system.

13. The method of claim 8, wherein the hydrogen pressure is between 20 psi and 75 psi.

14. The method of claim 13, wherein the hydrogen pressure is between 20 psi and 50 psi.

15. The method of claim 13, wherein the hydrogen pressure is between 50 psi and 75 psi.

* * * * *